(12) United States Patent
Meerpoel et al.

(10) Patent No.: US 6,262,052 B1
(45) Date of Patent: Jul. 17, 2001

(54) AMINO ACID ESTER CONTAINING AZOLE ANTIFUNGALS

(75) Inventors: Lieven Meerpoel, Beerse; Jan Heeres, Vosselaar; Robert Jozef Maria Hendrickx, Beerse, all of (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 09/355,369

(22) PCT Filed: Feb. 3, 1998

(86) PCT No.: PCT/EP98/00646

§ 371 Date: Jul. 26, 1999

§ 102(e) Date: Jul. 26, 1999

(87) PCT Pub. No.: WO98/34934

PCT Pub. Date: Aug. 13, 1998

(30) Foreign Application Priority Data

Feb. 11, 1997 (EP) .................................................. 97200374
Oct. 15, 1997 (EP) .................................................. 97203228

(51) Int. Cl.[7] ....................... A61K 31/496; C07D 405/14
(52) U.S. Cl. ..................................... 514/235.8; 514/236.2; 514/252.11; 514/253.09; 514/254.07; 544/121; 544/357; 544/364; 544/366; 544/370
(58) Field of Search ..................................... 544/366, 370, 544/357, 364, 121; 514/254.07, 235.8, 236.2, 252.11, 253.09

(56) References Cited

U.S. PATENT DOCUMENTS 4,791,111 * 12/1988 Heeres et al. ......................... 514/252

FOREIGN PATENT DOCUMENTS

| WO 95/17407 | 6/1995 | (WO) . |
| WO 95/19983 | 7/1995 | (WO) . |
| WO 96/38443 | 12/1996 | (WO) . |
| WO 97/00255 | 1/1997 | (WO) . |

* cited by examiner

*Primary Examiner*—Emily Bernhardt
(74) *Attorney, Agent, or Firm*—Mary Appollina

(57) ABSTRACT

The present invention concerns novel compounds of formula

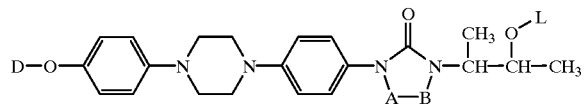

(I)

the N-oxide forms, the pharmaceutically acceptable addition salts thereof and stereochemically isomeric forms thereof, wherein —A—B— forms a bivalent radical of formula —N═CH— (a), —CH═N— (b), —CH═CH— (c), L represents the acyl moiety of an amino acid; D is an azole containing 1,3- or 1,4-dioxolane derivative as broad-spectrum antifungals; their preparation, compositions containing them and their use as a medicine.

13 Claims, No Drawings

AMINO ACID ESTER CONTAINING AZOLE ANTIFUNGALS

CROSS REFERENCE TO RELATED APPLICATIONS

This application is a National Stage application under 35 U.S.C. 371 of PCT/EP98/00646 filed Feb. 3, 1998, which claims priority from EP97.200.374.3, filed Feb. 11, 1997, and EP97.203.228.8, filed Oct. 15, 1997.

The present invention is concerned with novel broad-spectrum azole antifungals and their preparation; it further relates to compositions comprising them, as well as their use as a medicine.

Systemic fungal infections in man are relatively rare in temperate countries and many of the fungi that can become pathogenic normally live commensally in the body or are common in the environment. However, the past few decades have witnessed an increasing incidence of numerous life-threatening systemic fungal infections world-wide and these now represent a major threat to many susceptible patients, particularly those already hospitalized. Most of the increase can be attributed to improved survival of immunocompromised patients and the chronic use of antimicrobial agents. Moreover, the flora typical of many common fungal infections is also changing and this is presenting an epidemiological challenge of increasing importance. Patients at greatest risk include those with impaired immune functioning, either directly as a result of immunosuppression from cytotoxic drugs or HIV infection, or secondary to other debilitating diseases such as cancer, acute leukaemia, invasive surgical techniques or prolonged exposure to antimicrobial agents. The most common systemic fungal infections in man are candidosis, aspergillosis, histoplasmosis, coccidioidomycosis, paracoccidioidomycosis, blastomycosis and cryptococcosis.

Antifungals such as ketoconazole, itraconazole and fluconazole are employed for the treatment and prophylaxis of systemic fungal infections in immunocompromised patients. However, concern is growing about fungal resistance to some of these agents, especially these with a more narrow spectrum, e.g. fluconazole. Worse still, it is recognized in the medical world that about 40% of the people suffering from severe systemic fungal infections are hardly, or not at all, able to receive medication via oral administration. This inability is due to the fact that such patients are in coma or suffer from severe gastroparesis. Hence the use of insoluble or sparingly soluble antifungals such as itraconazole, that are difficult to administer intravenously, is heavily impeded in said group of patients.

Consequently, there is a need for new antifungals, preferably broad-spectrum antifungals, against which there is no existing resistance and which can be administered intravenously. Preferably the antifungal should also be available in a pharmaceutical composition suitable for oral administration. This enables the physician to continue treatment with the same drug after the patient has recovered from the condition which required intravenous administration of said drug.

U.S. Pat. No. 4,267,179 discloses heterocyclic derivatives of (4-phenylpiperazin-1-yl-aryloxy-methyl-1,3-dioxolan-2-yl)-methyl-1H-imidazoles and 1H-1,2,4-triazoles useful as antifungal agents. Said patent encompasses itraconazole, which is now available as a broadspectrum antifungal on a world-wide basis.

U.S. Pat. No. 4,916,134 teaches 4-[4-[4-[[2-(2,4-difluorophenyl)-2-(1H-azolylmethyl)-1,3-dioxolan-4-yl]methoxy]phenyl]-1-piperazinyl]phenyl]triazolones having improved antimicrobial properties.

U.S. Pat. No. 4,791,111 discloses derivatives of [[4-[4-(4-phenyl-1-piperazinyl)phenoxymethyl]-1,3-dioxolan-2-yl]methyl]-1H-imidazoles and 1H-1,2,4-triazoles, structurally related to some of the compounds of the present invention, which are taught to have favourable antimicrobial properties. A particular compound disclosed herein is cis-4-[4-[4-[4-[[2-(2,4-difluorophenyl)-2-(1H-1,2,4-triazol-1-ylmethyl)-1,3-dioxolan-4-yl]-methoxy]-phenyl]-1-piperazinyl]phenyl]-2,4-dihydro-2-(2-hydroxy-1-methylpropyl)-3H-1,2,4-triazol-3-one, said compound being a stereoisomeric mixture of all possible enantiomers and diastereomers having the cis configuration at the 1,3-dioxolane ring.

WO 93/19061 discloses the [2R-[2α,4α,4(R*)]], [2R-[2α,4α,4(S*)]], [2S-[2α,4α,4(S*)]] and [2S-[2α,4α,4(R*)]] stereospecific isomers of itraconazole, which are taught to have greater water solubility than the respective diastereomeric mixtures thereof.

WO 95/19983 discloses derivatives of [[4-[4-(4-phenyl-1-piperazinyl) phenoxy-methyl]-1,3-dioxolan-2-yl]methyl]-1H-imidazoles and 1H-1,2,4-triazoles, structurally related to some of the compounds of the present invention, which are taught to be water-soluble antimicrobial agents.

WO 95/17407 discloses tetrahydrofuran antifungals as well as WO 96/38443 and WO 97/00255. The latter two publications discloses tetrahydrofuran antifungals, which are taught to be soluble and/or suspendible in an aqueous medium suitable for IV, containing substitution groups readily convertible in vivo into hydroxy groups.

The present invention concerns novel compounds of formula

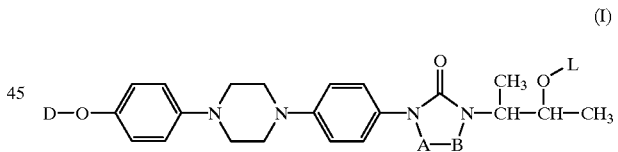

(I)

the N-oxide forms, the pharmaceutically acceptable addition salts and stereochemically isomeric forms thereof, wherein
—A—B— forms a bivalent radical of formula —N=CH— (a), —CH=N— (b), —CH=CH— (c), wherein one hydrogen atom in the radicals (a) and (b) may be replaced with a $C_{1-6}$alkyl-radical and up to two hydrogen atoms in radical (c) may be replaced by a $C_{1-6}$alkyl-radical;

L represents the acyl moiety of an amino acid, and thus —O—L represents an amino acid ester group;
D is a radical of formula

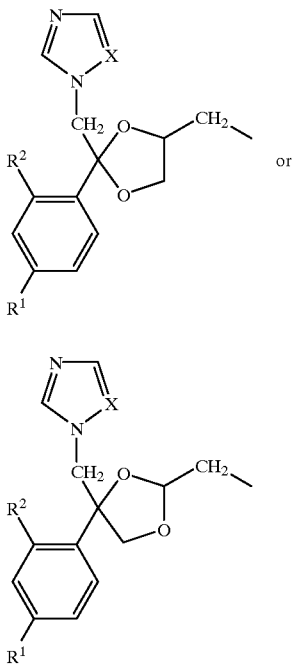

wherein
X is N or CH;
R$^1$ is halo;
R$^2$ is hydrogen or halo.

In the definitions hereinabove and hereinafter the term halo defines fluoro, chloro, bromo and iodo; C$_{1-6}$alkyl is generic to straight and branch chained hydrocarbons having from 1 to 6 carbon atoms, such as, for example, methyl, ethyl, propyl, butyl, pentyl or hexyl and the possible branched isomers thereof.

In the definition of L, the term "amino acid" is meant to include, but not limited to, the 20 α-amino acids commonly found in proteins such as, glycine, alanine, valine, leucine, isoleucine, methionine, proline, phenylalanine, tryptophan, serine, threonine, cysteine, tyrosine, asparagine, glutamine, aspartic acid, glutamic acid, lysine, arginine and histidine; and, amino acids of relatively rare occurrence which have been identified in specialized types of proteins such as, for example, 4-hydroxyproline, hydroxylysine, desmosine and isodesmosine; and, over 150 other amino acids occuring biologically in free or combined form but never in proteins whether they are α-, β-, γ- and δ-amino acids or whether they have a L- or D-configuration such as, for example, β-alanine, homocysteine and homoserine, citrulline, ornithine, γ-aminobutyric acid, D-glutamic acid and D-alanine; and synthetic amino acid analogues, such as, for example, phenylglycine, β-fluorophenylalanine, thionine, norleucine and the like.

In the definition of L, the term "amino acid" is also meant to include those amino acids in which the amino moiety is mono- or disubstituted; in such instances L may be represented by —L'—NR$_x$R$_y$. Examples of R$_x$ and R$_y$ include hydrogen, C$_{1-6}$alkyl and art-known protective groups for the amino moiety, e.g. tert-butyloxycarbonyl, benzyloxycarbonyl, trifluoromethoxycarbonyl or those protective groups mentioned in Chapter 7 of "Protective Groups in Organic Synthesis" by T. Greene and P. Wuyts (John Wiley & Sons, Inc. 1991). R$_x$ and R$_y$ may also form together with the nitrogen atom of the amino moiety of the amino acid a ring such as, for example, a pyrrolidine, piperidine, morpholine, piperazine or substituted piperazine ring, said substituted piperazine being a piperazine ring substituted on the 4-position of the piperazine ring with, for instance, C$_{1-6}$alkyl, hydroxyC$_{1-6}$alkyl, aminoC$_{1-6}$alkyl, mono- or dC$_{1-6}$alkyl)aminoC$_{1-6}$alkyl. For instance, in the case L is the acyl moiety of N,N-diethylglycine, then L'-represents —(=O)—CH$_2$— and —NR$_x$R$_y$ represents —CH$_2$CH$_3$)$_2$.

Many amino acids are commercially available and are listed in Novabiochem's 1997/1998 Catalog & Peptide Synthesis Handbook (Calbiochem-Novabiochem AG, Läufelfingen, Switzerland). Also these commercially available amino acids are meant to be included in the term "amino acid" as used in the definition of L.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term addition salt also comprises the hydrates and solvent addition forms which the compounds of formula (I) are able to form. Examples of such forms are e.g. hydrates, alcoholates and the like.

Suitable salt forms of the present compounds include the fumaric-, succinic-, L-malic-, oxalic-, maleic-, L-tartaric and hydrochloric acid salt form as well as the hydrated forms.

The term "stereochemically isomeric forms" as used hereinbefore defines all the possible stereoisomeric forms in which the compounds of formula (I) may exist, thus, also including all enantiomers, enantiomeric mixtures and diastereomeric mixtures. Unless otherwise mentioned or indicated, the chemical designation of compounds denotes the mixture of all possible stereochemically isomeric forms, said mixtures containing all diastereomers and enantiomers of the basic molecular structure. The same applies to the intermediates as described herein, used to prepare endproducts of formula (I).

Pure enantiomerically forms of the compounds and intermediates as mentioned herein are defined as enantiomers substantially free of other enantiomeric or diastereomeric forms of the same basic molecular structure of said compounds or intermediates.

Asymmetric centers may have the R- or S-configuration. The terms cis and trans are used herein in accordance with Chemical Abstracts nomenclature and refer to the position of the substituents on a ring moiety, more in particular on the dioxolane ring in the compounds of formula (I). In the latter instance, when establishing the cis or trans configuration, the substituent with the highest priority on the carbon atom in the 2 position of the dioxolane ring, and the substituent with the highest priority on the carbon atom in the 4 position of the dioxolane ring are considered (the priority of a substituent being determined according to the Cahn-Ingold-Prelog sequence rules). When said two substituents with highest priority are at the same side of the ring then the configuration is designated cis, if not, the configuration is designated trans.

The compounds of formula (I) all contain at least 4 asymmetric centers. As used herein, the stereochemical descriptors denoting the stereochemical configuration of each of the 4 or more asymmetric centers are also in accordance with Chemical Abstracts nomenclature. For instance, the absolute configuration of the asymmetric carbon atoms of compound 23 as described in example B.2 hereinafter, i.e. [2S-[2α,4α[(R*,R*)]]]-2-[4-[4-[4-[4-[[2-(2,4-diluorophenyl)-2-(1H-,2,4-triazol-1-ylmethyl)-1,3-dioxolan-4-yl]methoxy]-phenyl]-piperazinyl]-phenyl]-4,5-dihydro-5-oxo-1H-1,2,4-triazol-1-yl]-1-methylpropyl L-phenylalanine, is as depicted hereinbelow. The dioxolane ring in this compound has the cis configuration.

tor of intermediate 2i, i.e. [2α,4α(R*,R*)] indicates that intermediate 2i is a mixture of two enantiomers having respectively [2S-[2α,4α(R*,R*)]] and [2R-[2α,4α(R*,R*)]] as stereochemical descriptor.

Ring numbering on the dioxolane ring according to the Chemical Abstracts nomenclature is given for radicals D1 and D2 just below.

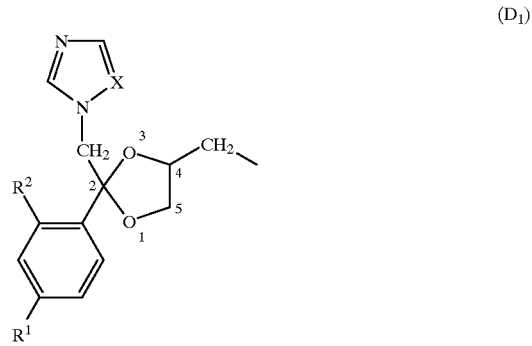

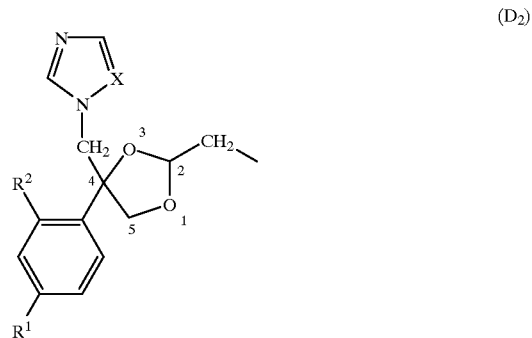

Of some compounds of formula (I) and of intermediates used in their preparation, the absolute stereochemical configuration was not experimentally determined. In those cases the stereochemically isomeric form which was first isolated is designated as "A" and the second as "B", without further reference to the actual stereochemical configuration.

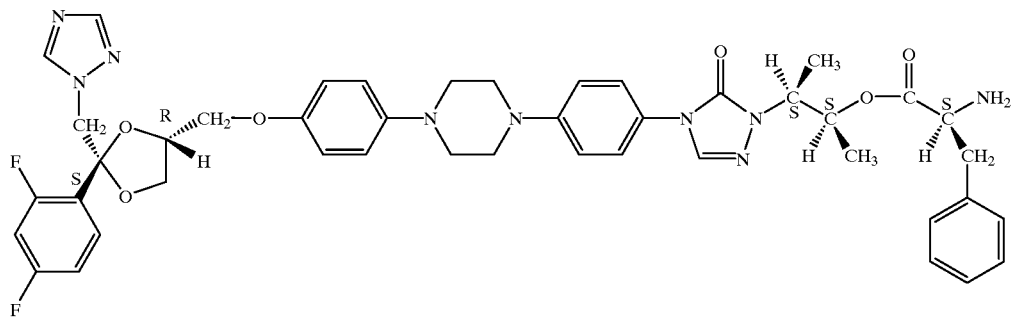

Further in accordance with Chemical Abstracts nomenclature, the name of a radical followed by the name of an amino acid refers to an ester wherein the amino acid is the acyl group. For example, in compound 23, L-phenylalanine is esterified with the said substituted 1-methylpropyl group.

The same Chemical Abstracts nomenclature is used to designate enantiomeric mixtures. For instance, the descrip- However, said "A" and "B" isomeric forms can be unambiguously characterized by for instance their optical rotation in case "A" and "B" have an enantiomeric relationship. A person skilled in the art is able to determine the absolute configuration of such compounds using art-known methods such as, for example, X-ray diffraction.

For example, intermediate 2b having the stereochemical descriptor [2S-[2α,4α[A-(R*,S*)]]] denotes the enantiomer having either the [2S-[2α,4α[(R*,S*)]]] or the [2S-[2α,4α[(S*,R*)]]] configuration, and is unambigously characterized by its optical rotation being $[\alpha]_{20}^{D}=-17.79°$ (c=49.75 mg/5m1 N,N-dimethylformamide).

The N-oxide forms of the present compounds are meant to comprise the compounds of formula (I) wherein one or several nitrogen atoms are oxidized to the so-called N-oxide.

Whenever used hereinafter, the term "compounds of formula (I)" is meant to also include their N-oxide forms, their pharmaceutically acceptable addition salts, and their stereochemically isomeric forms.

Within the scope of the present invention, —A—B— is suitably a radical of formula (b).

D is suitably a radical of formula D1.

X is suitably N.

$R^1$ and $R^2$ suitably are identical, preferably chloro or fluoro. In particular, both $R^1$ and $R^2$ are fluoro.

An interesting group of compounds within the present invention are those compounds of formula (I) wherein L represents a radical of formula (a)

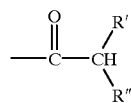

(a)

wherein

R' represents amino; mono- or d$C_{1-6}$alkyl)amino; amino$C_{1-6}$alkyl;

$C_{1-6}$alkyloxycarbonylamino; benzyloxycarbonylamino; trifuoromethoxycarbonylamino; 1-pyrrolidinyl; 1-piperidinyl; 4-morpholinyl;

1-piperazinyl or 1-piperazinyl substituted with $C_{1-6}$alkyl, hydroxy$C_{1-6}$alkyl, amino$C_{1-6}$alkyl or $C_{1-6}$alkylamino$C_{1-6}$alkyl;

R" represents hydrogen; $C_{1-6}$alkyl; aryl; $C_{1-6}$alkyl substituted with aryl, $C_{1-6}$alkylthio, indolyl, amino, hydroxy, mercapto, aminocarbonyl, carboxyl, guanidinyl, imidazolyl; or R' and R" taken together form —$CH_2$—$CH_2$—$CH_2$—NH—;

aryl is phenyl or phenyl substituted with hydroxy or halo.

A more interesting group contains those compounds of formula (I) wherein L represents the acyl moiety of one of the following amino acids:

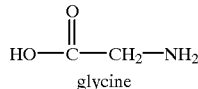
glycine

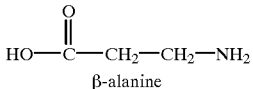
β-alanine

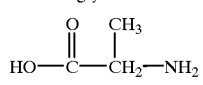
alanine

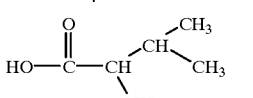
valine

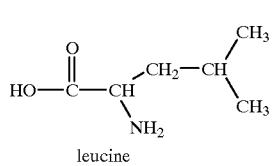
leucine

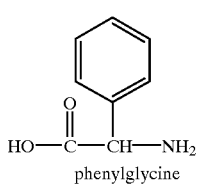
phenylglycine

-continued

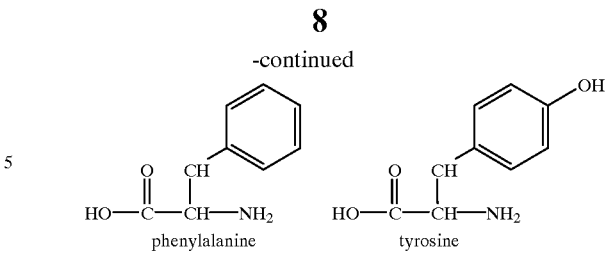
phenylalanine tyrosine or those derivatives thereof in which the amino moiety is mono- or disubstituted with $C_{1-6}$alkyl or mono-substituted with tert-butyloxycarbonyl.

Particularly interesting acyl moieties are those originating from alanine, β-alanine, glycine, leucine, valine, phenylglycine, phenylalanine and their N-tert-butyloxycarbonyl derivative, and N,N-diethylglycine and N,N-diethyl-β-alanine; especially, glycine, β-alanine, L-alanine, L-valine, L-leucine, L-phenylglycine, L-phenylalanine, D-phenylalanine, N-((1,1-dimethylethyl)oxycarbonyl)-β-alanine, N-((1,1-dimethylethyl)oxycarbonyl)-glycine, N,N-diethyl-glycine, N,N-diethyl-β-alanine, N-((1,1-dimethylethyl)oxy-carbonyl)-L-alanine, N-((1,1-dimethylethyl)oxy-carbonyl)-L-leucine, N-((1,1-dimethylethyl)oxy-carbonyl)-L-phenyl-glycine, N-((1,1-dimethylethyl)oxy-carbonyl)-L-valine, N-((1,1-dimethylethyl)oxy-carbonyl)-L-phenyl-alanine, N-((1,1-dimethylethyl)oxy-carbonyl)-D-phenyl-alanine.

Particular compounds are those compounds of formula (I) wherein D is a radical of formula D1 wherein X is N and $R^1$ and $R^2$ are both fluoro; and —A—B— is a radical of formula (b); and L represents the acyl moiety of leucine, valine, phenylglycine, phenylalanine and their N-tert-butyloxycarbonyl derivative; or L represents the acyl moiety of N,N-diethylglycine.

Other particular compounds are those compounds of formula (I) wherein D, whether it is D1 or D2, has a cis configuration.

Preferred compounds are those compounds wherein D is a radical of formula D1 wherein the substituents on the dioxolane ring have a cis configuration and carbon atom number 2 of the dioxolane ring has an absolute S configuration as depicted hereinbelow.

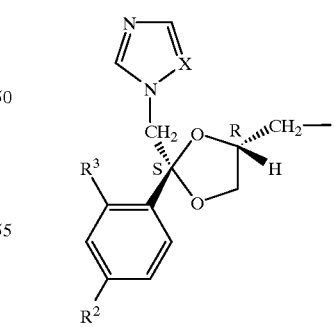

(D1)

Other preferred compounds are those compounds wherein the 1-methylpropyl moiety has a threo configuration, i.e. the two chiral carbons of the 1-methylpropyl moiety (both chiral carbon atoms are marked with an asterisk in the figure hereinbelow) have identical absolute configura-tions, e.g. they both have the R configuration or they both have the S configuration.

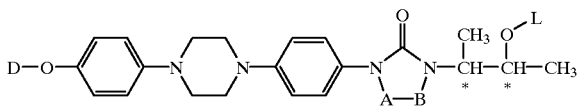

More preferred compounds are the compounds of formula (I) in their enantiomerically pure forms, in particular those compounds of formula (I) wherein the two chiral carbons of the 1-methylpropyl moiety both have the S configuration, and D is a radical of formula D1 wherein the substituents on the dioxolane ring have a cis configuration and carbon atom number 2 of the dioxolane ring has an absolute S configuration, which corresponds to those compounds of formula (I) wherein D is a radical of formula D1 having the [2S-[2α,4α[(R*,R*)]]] configuration.

Most preferred are the compounds;

2-[4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-4,5-dihydro-5-oxo-1H-1,2,4-triazol-1-yl]-1-methylpropyl N,N-diethylglycine;

2-[4-[4-[4-[4-[[2-(2,4-difluorophenyl)-2-(1H-1,2,4-triazol-1-ylmethyl)-1,3-dioxolan-4-yl]methoxy]-phenyl]-1-piperazinyl]-phenyl]-4,5-dihydro-5-oxo-1H-1,2,4-triazol-1-yl]-1-methylpropyl L-phenylalanine;

2-[4-[4-[4-[4-[[2-(2,4-difluorophenyl)-2-(1H-1,2,4-triazol-1-ylmethyl)-1,3-dioxolan-4-yl]methoxy]-phenyl]-1-piperazinyl]-phenyl]-4,5-dihydro-5-oxo-1H-1,2,4-triazol-1-yl]1-methylpropyl L-leucine;

2-[4-[4-[4-[4-[[2-(2,4-difluorophenyl)-2-(1H-i ,2,4-triazol-1-ylmethyl)-1,3-dioxolan-4-yl]methoxy]-phenyl]-1-piperazinyl]-phenyl]-4,5-dihydro-5-oxo-1H-1,2,4-triazol-1-yl]-1-methylpropyl L-valine;

2-[4-[4-[4-[4-[[2-(2,4-difluorophenyl)-2-(1H-1,2,4-triazol-1-ylmethyl)-1,3-dioxolan-4-yl]methoxy]-phenyl]-1-piperazinyl]-phenyl]-4,5-dihydro-5-oxo-1H-1,2,4-triazol-1-yl]-1-methylpropyl L-phenylglycine; the N-oxide forms, the pharmaceutically acceptable addition salts thereof and the stercochemical isomeric forms thereof, especially their [2S-[2α,4α[(R*,R*)]]] form.

The meaning of the variables as used in the following reaction procedures is as defined hereinabove, unless otherwise stated.

The compounds of the present invention may be prepared using art-known esterification methods e.g., those described in "Principles of Peptide Synthesis", M. Bodanszky, Springer-Verlag Berlin Heidelberg, 1984. Particular reaction procedures are described hereinbelow.

The compounds of formula (I) may generally be prepared by O-acylation of an intermediate alcohol of formula (II) with an acylating reagent of formula (III), wherein $W^1$ is a reactive leaving group such as, halo, azido or an activated acid function, e.g. a halophenyl ester such as a pentachloro- or pentafluorophenyl ester, and is connected to the acyl moiety of L. Said reaction may be performed following art-known acylation procedures, for instance, by stirring the reactants in a reaction-inert solvent, optionally in admixture with a base to pick up the acid that is formed during the reaction. Alternatively, the O-acylation is done by using a suitable coupling reagent such as dicyclohexylcarbodiimide or a functional derivative thereof.

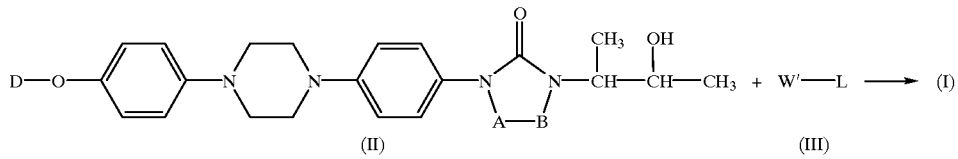

In this and the following preparations, the reaction products may be isolated from the reaction medium and, if necessary, further purified according to methodologies generally known in the art such as, for example, extraction, crystallization, trituration and chromatography.

The compounds of formula (I) may also be prepared by O-alkylating a phenol of formula (IV) with an alkylating reagent of formula (V), wherein $W^2$ is a reactive leaving group such as halo, or a sulfonyloxy group. Said reaction may be performed by stirring the reactants in a reaction-inert solvent, optionally in admixture with a suitable base to pick up the acid that is formed during the reaction. In the compounds and intermediates mentioned hereinafter the substituents are as defined above, unless otherwise indicated.

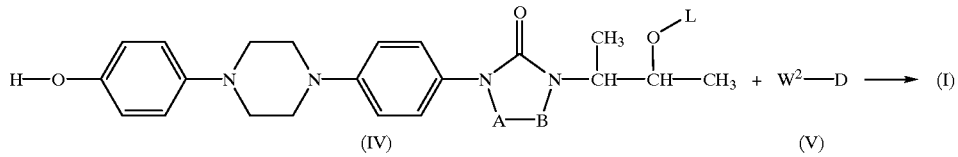

The preparation of intermediates of formula (V), wherein D is a radical of formula D1, has been disclosed in U.S. Pat. No. 4,267,179.

As defined hereinabove, the variable L may also be represented by L'-$NR_xR_y$ of which the two moieties, i.e. L'- and —$NR_xR_y$ are used in the following reaction scheme.

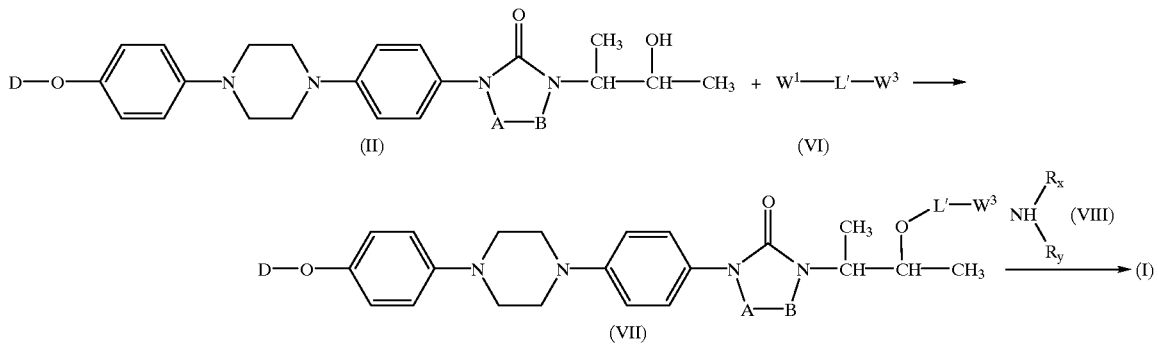

(II)  (VI)  (VII)  (I)

The above reaction scheme depicts the preparation of the compounds of formula (I) by O-acylating an intermediate of formula (II) with a reagent of formula (VI), wherein $W^3$ is a reactive leaving group such as halo, and $W^1$ is as defined hereinabove and is connected to the acyl moiety L'; and subsequently reacting the thus obtained intermediate of formula (VII) with an amine of formula (VIII).

The compounds of formula (I) may also be converted into each other following art-known transformations. For instance, compounds of formula (I) wherein L contains a protected amino moiety may be converted to compounds of formula (I) wherein said amino moiety is unsubstituted, using art-known deprotection procedures, e.g. by reaction with trifluoroacetic acid in an appropriate solvent, e.g. dichloromethane.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Some of the intermediates and starting materials used in the above reaction procedures are commercially available, or may be synthesized according to procedures described elsewhere, e.g. U.S. Pat. No. 4,791,111, U.S. Pat. No. 4,931,444 and U.S. Pat. No. 4,267,179. Some methods of preparing the intermediates of the present invention are described hereinbelow.

For instance, the intermediates of formula (II) may be prepared by O-alkylating a reagent of formula (IX) with an alkylating reagent of formula (V) following O-alkylation procedures described hereinabove for the preparation of compounds of formula (I).

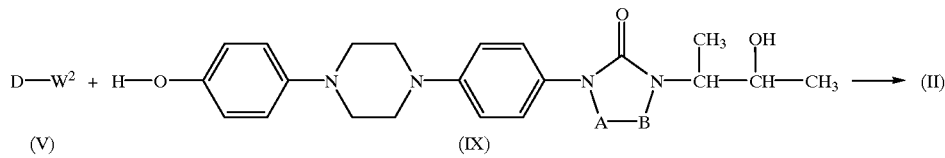

(V)  (IX)  (II)

The intermediates of formula (II) may also be prepared by O-alkylating a reagent of formula (X) with an alkylating reagent of formula (V) following O-alkylation procedures described hereinabove for the preparation of compounds of formula (I), and subsequently reducing the thus formed intermediate of formula (XI). Said reduction may be performed by stirring the intermediate of formula (XI) with a reducing reagent, such as, for example, sodiumborohydride in a reaction-inert solvent, such as, for example, dichloromethane, methanol or mixtures thereof.

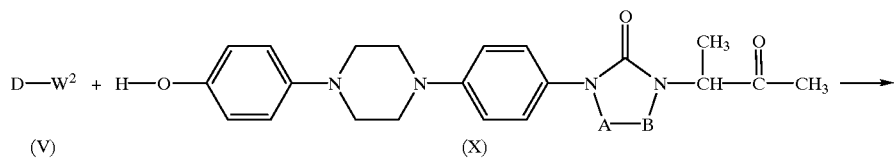

(V)  (X)

-continued

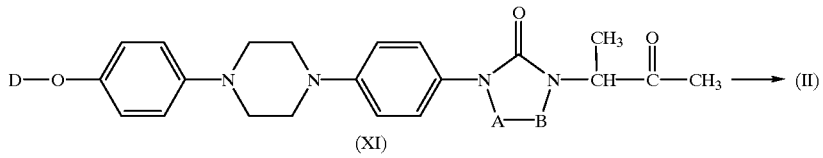

The preparation of intermediates of formula (X) is disclosed in U.S. Pat. No. 4,931,444.

The intermediates of formula (XI) may also be prepared by N-alkylating an intermediate of formula (XII) following art-known N-alkylation procedures with an alkylating reagent of formula (XIII), wherein $W^4$ is an appropriate leaving group, e.g. halo.

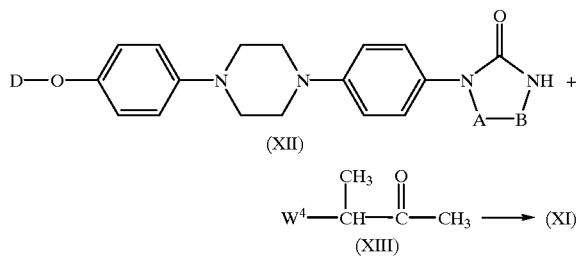

Pure stereochemically isomeric forms of the compounds and the intermediates of this invention may be obtained by the application of art-known procedures. Diastereomers may be separated by physical separation methods such as selective crystallization and chromatographic techniques, e.g. liquid chromatography. Enantiomers may be separated from each other by the selective crystallization of their diastereomeric salts with optically active acids. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereoselectively or stereospecifically. Preferably if a specific stereoisomer is desired, said compound will be synthesized by stereoselective or stereospecific methods of preparation.

These methods will advantageously employ enantiomerically pure starting materials. Stereochemically isomeric forms of the compounds of formula (I) are obviously intended to be included within the scope of the invention.

As stated hereinabove, the enantiomerically pure forms of the compounds of formula (I) form a preferred group of compounds. It is therefore that the enantiomerically pure forms of the intermediates of formula (II), their N-oxide forms and their addition salt forms are particularly useful in the preparation of enantiomerically pure compounds of formula (I). Also enantiomeric mixtures and diastereomeric mixtures of intermediates of formula (II) are useful in the preparation of compounds of formula (I) with the corresponding configuration. Said enantiomerically pure forms and also the enantiomeric and diastereomeric mixtures of the intermediates of formula (II) are deemed novel.

4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-(2-hydroxy-1-methylpropyl)-3H-1,2,4-triazol-3-one in its [2S-[2α,4α [(R*,R*)]]] enantiomerically pure form and the corresponding 2,4-dichlorophenyl analogue are particularly preferred intermediates of formula (II).

In particular, the [2S-[2α,4α[(R*,R*)]]] pure enantiomeric form of intermediates of formula (II) can be prepared by reacting the corresponding enantiomerically pure form of intermediate (IX), i.e. the [S-(R*,R*)] form, being represented by formula (IX-a), with the corresponding enantiomerically pure form of intermediate (V), i.e. the [2S-(2α, 4α)] form, being represented by (V-a), according to the reaction procedure as described above.

The stereoselective synthesis of intermediate (IX-a) starting from intermediate (X) can be performed as depicted in scheme 1.

Scheme 1

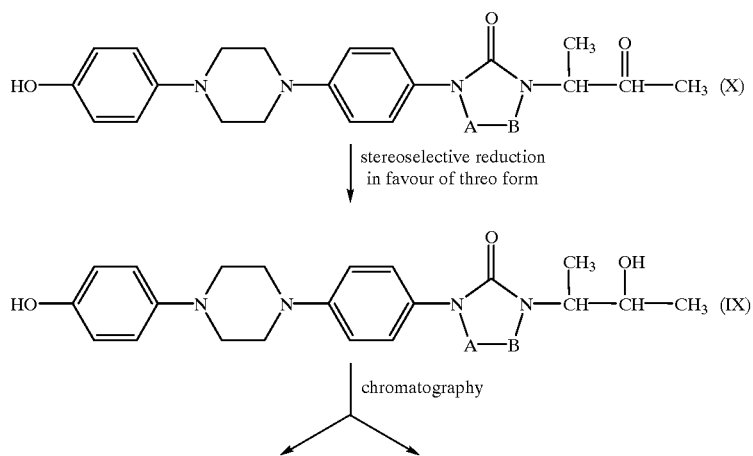

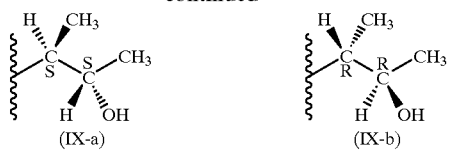

(IX-a)    (IX-b)

Suitable stereoselective reduction conditions include the use of K-selectride in a suitable solvent such as, for example, dimethylacetamide or tetrahydrofuran; the use of sodium-borohydride optionally in combination with $CeCl_3.7H_2O$, $ZnCl_2$ or $CaCl_2.2H_2O$ in a suitable solvent such as, for example, dimethylacetamide, dimethylformamide, methanol or tetrahydrofuran. Said reduction conditions favour the threo form of the 2-hydroxy-1-methylpropyl moiety, i.e. the form where the two asymmetric carbon atoms have identical absolute configuration. Recrystallisation of the obtained mixture after stereoselective reduction may even further improve the ratio threo/erythro in favor of the threo form. The desired [S-(R*,R*)] form can then be isolated chromatographically using a chiral stationary phase such as, for example, Chiralpak AD (amylose 3,5 dimethylphenyl carbamate) purchased from Daicel Chemical Industries, Ltd, in Japan.

The alkoxyphenyl derivatives of the intermediates of formula (IX-a) may be prepared according to the same reaction procedures as in scheme 1.

An alternative way to prepare intermediates of formula (IX-a), or the alkoxyphenyl analogues thereof, is as depicted in scheme 2.

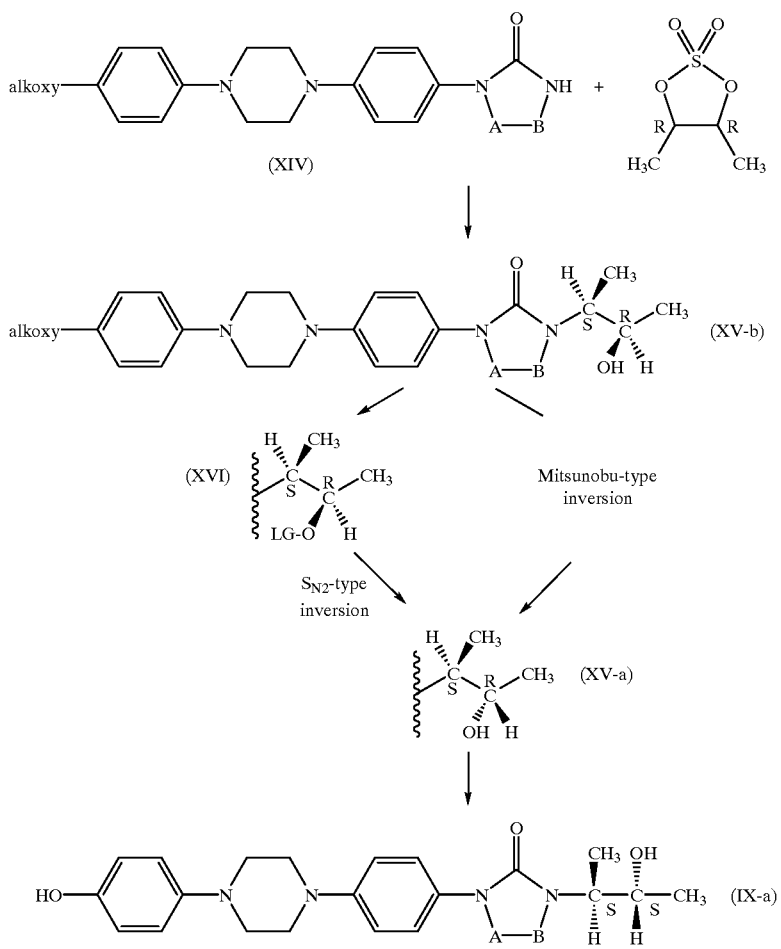

The reaction of an intermediate of formula (XIV) with (4R-trans)-4,5-dimethyl-2,2-dioxide-1,3,2-dioxathiolane may be performed in a suitable solvent, preferably a polar aprotic solvent such as, for example, dimethylacetamide or N,N-dimethylformamide, and in the presence of a base such as, for example, potassium tert-butanolate, potassium hydroxide or potassium hydride. Subsequently, an acid such as, sulfuric acid, may be added to the reaction mixture, thus obtaining an intermediate of formula (XV-b) whereby the 2-hydroxy-1-methylpropyl moiety has the erythro form. Then, the carbon atom bearing the alcohol function of said 2-hydroxy-1-methylpropyl moiety is epimerized, preferably 100% inverted, thus obtaining intermediate (XV-a) whereby the 2-hydroxy-1-methylpropyl moiety has the threo form. Two pathways are convenient.

A first pathway involves the transformation of the alcohol function into a suitable leaving group O-LG by, for instance, derivatizing the hydroxy group with an organic acid such as, for example, a carboxylic acid, e.g. acetic acid or 4-nitrobenzoic acid; or a sulfonic acid, e.g. β-toluenesulfonic acid or methanesulfonic acid; thus obtaining an intermediate of formula (XVI). The carbon atom bearing the leaving group in said intermediate (XVI) may subsequently be epimerized, preferably 100% inverted, by a $S_{N2}$-type reaction with a suitable nucleophilic reagent such as, for example, a alcoholate, e.g. a benzyloxy group; an hydroxy salt of an alkali metal, e.g. sodiumhydroxide or potassium hydroxide; an acetate, e.g. sodium acetate. Said reaction is performed in a suitable solvent, preferably a polar aprotic solvent such as, for example, dimethylacetamide, N-methylpyrrolidinone, dimethylimidazolidinone or sulfolane. In case an alcoholate or an acetate is used in the $S_{N2}$ reaction, the thus obtained intermediate may be deprotected using art-known deprotection techniques, thus obtaining an alcohol intermediate of formula (XV-a).

An alternative pathway for inverting the stereochemistry of the carbon atom bearing the alcohol function is the use of the Mitsunobu reaction. The alcohol function of an intermediate of formula (XV-b) is activated with diisopropyl azodicarboxylate or a functional derivative thereof such as diethyl azodicarboxylate, in the presence of triphenylphosphine, and in a polar aprotic solvent such as, for example, dimethylacetamide or dimethylformamide. The thus obtained activated alcohol is subsequently reacted with a carboxylic acid such as, for example, 4-nitrobenzoic acid, acetic acid, monochloroacetic acid. The thus obtained ester whereby the 2-hydroxy-1-methylpropyl moiety has been transformed to the threo form may subsequently be hydrolized using art-known hydrolysis techniques, thus obtaining an intermediate of formula (XV-a).

Finally, the alkoxyphenyl moiety of the intermediates of formula (XV-a) may be transformed to the phenol moiety using for instance, bromic acid in acetic acid in the presence of sodium thiosulfate, thus obtaining an intermediate of formula (IX-a).

Suitable alternatives for (4R-trans)-4,5-dimethyl-2,2-dioxide-1,3,2-dioxathiolane include the following enantiomerically pure intermediates

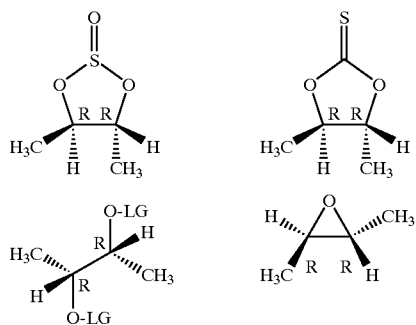

wherein LG is a leaving group such as, for example, β-toluenesulfonyl.

The intermediates of formula (IX-b), whereby the 2-hydroxy-1-methylpropyl moiety has the [R-(R*,R*)] form, may be prepared using the same reaction pathways as depicted in scheme 2 but replacing (4R-trans)-4,5-dimethyl-2,2-dioxide-1,3,2-dioxathiolane with its enantiomer (4S-trans)-4,5-dimethyl-2,2-dioxide-1,3,2-dioxathiolane.

Alternatively to the reaction pathway in scheme 2, an intermediate of formula (XIV) may be directly coupled with an enantiomerically pure intermediate such as [R-(R*,S*)]-3-bromo-2-butanol 4-nitrobenzoate or a functional derivative thereof, thus immediately obtaining an intermediate of formula (XV-a).

Interestingly, particular pure enantiomeric forms of the intermediates of formula (IV) may be synthesized using the Mitsunobu pathway in scheme 2 whereby the carboxylic acid, used in the reaction with the activated alcohol of formula (XV-b), is replaced with a protected amino acid. Optionally, the amino acid may be deprotected using art-known techniques.

The compounds of formula (1), the pharmaceutically acceptable addition salts and the stereochemically isomeric forms thereof are useful agents for combating fungi in vivo. Moreover, the solubility profile in aqueous solutions of the compounds of formula (I) makes them suitable for intravenous administration. The present compounds are found to be active against a wide variety of fungi, such as Candida spp., e.g. *Candida albicans, Candida glabrata, Candida krusei, Candicla parapsilosis, Candida kefyr, Candida tropicalis*; Aspergillus spp., e.g. *Aspergillus fumigatus, Aspergillus niger, Aspergillus flavus; Cryptococcus neoformans; Sporothrix schenckii*, Fonsecaea spp.; *Epidermophyton floccosum; Microsporum canis*; Trichophyton spp.; Fusarium spp.; and several dermatiaceous hyphomycetes.

Also, the pure enantiomers, the enantiomeric mixtures and the diastereomeric mixtures of the intermediates of formula (II) are antimycotics having a favourable pharmacological profile with respect to antifungal activity and adverse effects.

The chemical stability of some of the compounds of formula (I) has been determined as is shown in the experimental part hereinafter. Experiments show that metabolic degradation of the present compounds to the intermediates of formula (II) is organ specific and does not occur readily. Further, in vitro experiments indicate that the compounds of formula (1) have an improved intrinsic inhibitory capacity on fungal growth in for instance *Candida albicanis* when compared to the intermediates of formula (II), of which the antifungal activity is taught in U.S. Pat. No. 4,791,111. Said in vitro experiments include the determination of the fungal susceptibility of the present compounds as described in the pharmacological example hereinafter. Other in vitro experiments such as the determination of the effects of the present compounds on the sterol synthesis in, for instance, *Candida albicans*, demonstrate their antifungal potency. Also in vivo experiments in several mouse, guinea-pig and rat models show that, after both oral and intravenous administration, the present compounds are potent antifungals.

The compounds of the present invention also have a good oral availability.

In view of the utility of the compounds of formula (I), there is provided a method of treating warm-blooded animals, including humans, suffering from fungal infections. Said method comprises the systemic or topical administration of an effective amount of a compound of formula (I), a N-oxide form, a pharmaceutically acceptable addition salt or a possible stereoisomeric form thereof, to warm-blooded animals, including humans. Hence, compounds of formula (I) are provided for use as a medicine, in particular, the use of a compound of formula (I) in the manufacture of a medicament useful in treating fungal infections is provided.

The present invention also provides compositions for treating or preventing fungal infections comprising a therapeutically effective amount of a compound of formula (I) and a pharmaceutically acceptable carrier or diluent.

In view of their useful pharmacological properties, the subject compounds may be formulated into various pharmaceutical forms for administration purposes. To prepare the pharmaceutical compositions of this invention, a therapeutically effective amount of a particular compound, in base or addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, topically, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. As appropriate compositions for topical application there may be cited all compositions usually employed for topically administering drugs e.g. creams, gellies, dressings, shampoos, tinctures, pastes, ointments, salves, powders and the like. For parenteral compositions, the carrier will usually comprise sterile water, at least in large part, though other ingredients, to aid solubility for example, e.g. cyclodextrins, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. For parenteral compositions, the carrier will usually comprise sterile water, at least in large part. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. For parenteral compositions, other ingredients, to aid solubility for example, e.g. cyclodextrins, may be included. Appropriate cyclodextrins are $\alpha$-, $\beta$-, $\gamma$-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated $\beta$-CD; hydroxy$C_{1-6}$alkyl, particularly hydroxyethyl, hydroxypropyl or hydroxybutyl; carboxy$C_{1-6}$alkyl, particularly carboxymethyl or carboxyethyl; $C_{1-6}$alkylcarbonyl, particularly acetyl. Especially noteworthy as complexants and/or solubilizers are $\beta$-CD, randomly methylated $\beta$-CD, 2,6-dimethyl-$\beta$-CD, 2-hydroxyethyl-$\beta$-CD, 2-hydroxyethyl-$\gamma$-CD, 2-hydroxypropyl-$\gamma$-CD and (2-carboxymethoxy)propyl-$\beta$-CD, and in particular 2-hydroxypropyl-$\beta$-CD (2-HP-$\beta$-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those of skill in treating warm-blooded animals suffering from diseases caused by fungi could easily determine the therapeutically effective daily amount from the test results given herein. In general, it is contemplated that a therapeutically effective daily amount would be from 0.05 mg/kg to 20 mg/kg body weight.

Experimental Part

Hereinafter, "DMF" is defined as N,N-dimethylformamide, "MIK" is defined as methylisobutylketone, "DIPE" is defined as diusopropylether.

A. Preparation of the Intermediates

EXAMPLE A-1

A mixture of (±)-2,4-dihydro-4-[4-[4-(4-hydroxyphenyl)-1-piperazinyl]phenyl]-2-(1-methyl-2-oxopropyl)-3H-1,2,4-triazol-3-one (0.06 mol) in DMF (500 ml) was cooled to $-10°$ C. and then stirred under $N_2$ flow. Potassium tri-sec-butylborohydride, 1 M solution in tetrahydrofuran (150 ml) was added dropwise. The mixture was allowed to warm to room temperature slowly and then poured out into water. The precipitate was filtered off, washed with $CH_3OH$ and crystallized from $CH_3OH$. The precipitate was filtered off and dried. The residue was purified by HPLC over CHIRALPAC AD (eluent: ethanol). Two pure fractions were collected and their solvents were evaporated. Each residue was triturated in $CH_3OH$. The precipitate was filtered off and dried, yielding 7.3 g [S-(R*,R )] -2,4-dihydro-2-(2-hydroxy-1 methylpropyl)-4-[4-[4-(4-hydroxyphenyl)-1-piperazinyl]phenyl]-3H-1,2,4-triazol-3-one. (interm. 1a) $[\alpha]_{20}^D = -10.81°$ (c=50.43 mg/5 ml DMF).

In a similar way were prepared
[A-(R*,S*)]-2,4-dihydro-2-(2-hydroxy-1-methylpropyl)-4-[4-[4-(4-hydroxy-phenyl)-1-piperazinyl]phenyl]-3H-1,2,4-triazol-3-one (interm. 1b) $[\alpha]_{20}^D = -7.07°$ (c=48.8 mg/5 ml DMF);

[B-(R*,S*)]-2,4-dihydro-2-(2-hydroxy-1-methylpropyl)-4-[4-[4-(4-hydroxy-phenyl)-1-piperazinyl]phenyl]-3H-1,2,4-triazol-3-one (interm. 1c) $[\alpha]_{20}^{D}$=+6.86° (c=49.58 mg/5 ml DMF);

[R-(R*,R*)]-2,4-dihydro-2-(2-hydroxy-1-methylpropyl)-4-[4-[4-(4-hydroxy-phenyl)-1-piperazinyl]phenyl]-3H-1,2,4-triazol-3-one (interm. 1d) $[\alpha]_{20}^{D}$=+10.35° (c=48.81 mg/5 ml DMF);

(R*,S*)-2,4-dihydro-2-(2-hydroxy-1-methylpropyl)-4-[4-[4-(4-hydroxyphenyl)-1-piperazinyl]phenyl]-3H-1,2,4-triazol-3-one (interm. 1e).

In a similar way are also prepared (R*,R*)-2,4-dihydro-2-(2-hydroxy-1-methylpropyl)-4-[4-[4-(4-hydroxyphenyl)-1-piperazinyl]phenyl]-3H-1,2,4-triazol-3-one (interm. 1f);

[R-(R*,R*)+R-(R*,S*)]-2,4-dihydro-2-(2-hydroxy-1-methylpropyl)-4-[4-[4-(4-hydroxyphenyl)-piperazinyl]phenyl]-3H-1,2,4-triazol-3-one (interm. 1g);

[R-(R*,R*)+S-(R*,S*)]-2,4-dihydro-2-(2-hydroxy-1-methylpropyl)-4-[4-[4-(4-hydroxyphenyl)-1-piperazinyl]phenyl] -3H-1,2,4-triazol-3-one (interm. 1h);

[S-(R*,R*)+R-(R*,S*)]-2,4-dihydro-2-(2-hydroxy-1-methylpropyl)-4-[4-[4-(4-hydroxyphenyl)-1-piperazinyl]phenyl]-3H-1,2,4-triazol-3-one (interm. 1i);

[S-(R*,R*)+S-(R*,S*)]-2,4-dihydro-2-(2-hydroxy-1-methylpropyl)-4-[4-[4-(4-hydroxyphenyl)-1-piperazinyl]phenyl]-3H-1,2,4-triazol-3-one (interm. 1j);

EXAMPLE A-2

A mixture of cis-(2S) 4-methylbenzenesulfonate 2-(2,4-difluorophenyl)-2-(1H-1,2,4-triazol-1-ylmethyl)-1,3-dioxolane-4-methanol (ester) (0.0134 mol), intermediate (Ia) (0.0122 mol) and NaOH (0.013 mol) in DMF (200 ml) was stirred at 60° C. under $N_2$ flow overnight. The mixture was cooled and poured out into water. The precipitate was filtered off and dried. The residue was purified by column chromatography over silica gel (eluent: $CH_2Cl_2/CH_3OH$ 94/6 to 0/100). The pure fractions were collected and the solvent was evaporated. The residue was triturated in MIK. The precipitate was filtered off and dried, yielding 4.7 g (56%) [2S-[2α,4α[(R*,R*)]]]-4-[4-[4-[[2-(2,4-difluorophenyl)-2-(1H-1,2,4-triazol-1-ylmethyl)-1,3-dioxolan-4-yl]methoxy]-phenyl]-1-piperazinyl]phenyl]-2,4-dihydro-2-(2-hydroxy-1-methylpropyl)-3H-1,2,4-triazol-3-one. (interm. 2a) $[\alpha]_{20}^{D}$=−20.14° (c=49.49 mg/5 ml DMF).

Table I lists intermediates which were prepared analogously to example A.2. The asymmetric carbon atoms are marked a, b, c and d, their absolute configuration and optical rotation are also denoted in Table 1.

TABLE 1

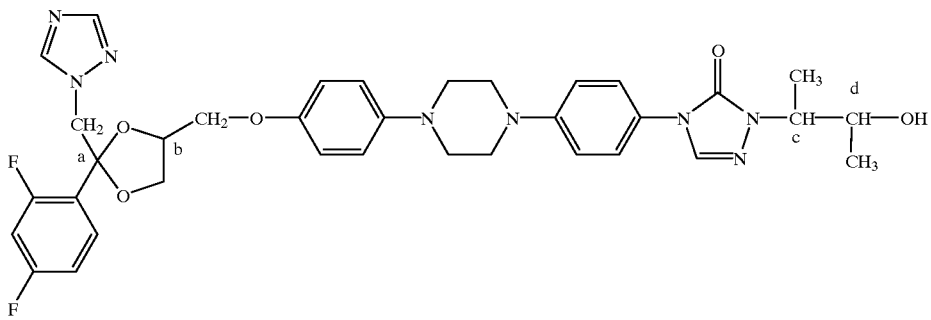

| Interm. No. | Chemical Abstracts descriptor | absolute configuration of carbon atom a,b,c,d | optical rotation as $[\alpha]_{20}^{D}$ @ concentration in DMF |
|---|---|---|---|
| 2a | [2S-[2α,4α(R*,R*)]] | S,R,S,S | −20.14° @ 49.49 mg/5 ml |
| 2b | [2S-[2α,4α[A-(R*,S*)]]] | S,R,R,S or S,R,S,R | −17.79° @ 49.75 mg/5 ml |
| 2c | [2S-[2α,4α[B-(R*,S*)]]] | S,R,S,R or S,R,R,S | −9.36° @ 50.77 mg/5 ml |
| 2d | [2S-[2α,4α(S*,S*)]] | S,R,R,R | −7.71° @ 48.61 mg/5 ml |
| 2e | [2R-[2α,4α[A-(R*,S*)]]] | R,S,R,S or R,S,S,R | +9.22° @ 51.52 mg/5 ml |
| 2f | [2R-[2α,4α[B-(R*,S*)]]] | R,S,S,R or R,S,R,S | +17.79° @ 49.76 mg/5 ml |
| 2g | [2R-[2α,4α(R*,R*)]] | R,S,R,R | +19.49° @ 51.81 mg/5 ml |
| 2h | [2R-[2α,4α(S*,S*)]] | R,S,S,S | +7.13° @ 49.77 mg/5 ml |

Table 2 list intermediates which are prepared analogously to example A.2.

TABLE 2

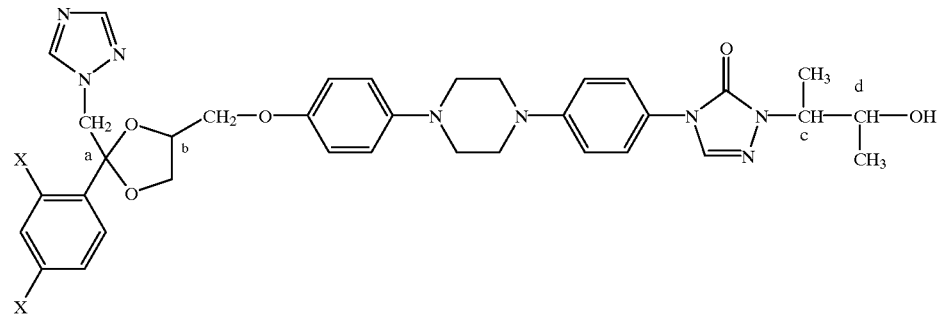

| Interm. No. | X | Chemical Abstracts descriptor | absolute configuration of carbon atom a,b,c,d |
|---|---|---|---|
| 2i | F | [2α,4α(R*,R*)] | S,R,S,S + R,S,R,R |
| 2j | F | [2α,4α(R*,S*)] | S,R,S,R + R,S,R,S |
| 2k | F | [2α,4α(S*,R*)] | S,R,R,S + R,S,S,R |
| 2l | F | [2α,4α(S*,S*)] | S,R,R,R + R,S,S,S |
| 2m | F | [2S-[2α,4α(R*,R*)]] + [2S-[2α,4α(R*,S*)]] | S,R,S,S + S,R,S,R |
| 2n | F | [2S-[2α,4α(R*,R*)]] + [2S-[2α,4α(S*,R*)]] | S,R,S,S + S,R,R,S |
| 2o | F | [2S-[2α,4α(R*,R*)]] + [2S-[2α,4α(S*,S*)]] | S,R,S,S + S,R,R,R |
| 2p | F | [2S-[2α,4α(R*,R*)]] + [2R-[2α,4α(R*,S*)]] | S,R,S,S + R,S,R,S |
| 2q | F | [2S-[2α,4α(R*,R*)]] + [2R-[2α,4α(S*,R*)]] | S,R,S,S + R,S,S,R |
| 2r | F | [2S-[2α,4α(R*,R*)]] + [2R-[2α,4α(S*,S*)]] | S,R,S,S + R,S,S,S |
| 2s | F | [2S-[2α,4α(S*,S*)]] + [2S-[2α,4α(R*,S*)]] | S,R,R,R + S,R,S,R |
| 2t | F | [2S-[2α,4α(S*,S*)]] + [2S-[2α,4α(S*,R*)]] | S,R,R,R + S,R,R,S |
| 2u | F | [2S-[2α,4α(S*,S*)]] + [2R-[2α,4α(R*,S*)]] | S,R,R,R + R,S,R,S |
| 2v | F | [2S-[2α,4α(S*,S*)]] + [2R-[2α,4α(S*,R*)]]] | S,R,R,R + R,S,S,R |
| 2w | F | [2S-[2α,4α(S*,S*)]] + [2R-[2α,4α(R*,R*)]] | S,R,R,R + R,S,R,R |
| 2x | F | [2R-[2α,4α(R*,R*)]] + [2S-[2α,4α(R*,S*)]] | R,S,R,R + S,R,S,R |
| 2y | F | [2R-[2α,4α(R*,R*)]] + [2S-[2α,4α(S*,R*)]] | R,S,R,R + S,R,R,S |
| 2z | F | [2R-[2α,4α(R*,R*)]] + [2R-[2α,4α(R*,S*)]] | R,S,R,R + R,S,R,S |
| 2aa | F | [2R-[2α,4α(R*,R*)]] + [2R-[2α,4α(S*,R*)]] | R,S,R,R + R,S,S,R |
| 2ab | F | [2R-[2α,4α(R*,R*)]] + [2R-[2α,4α(S*,S*)]] | R,S,R,R + R,S,S,S |
| 2ac | F | [2R-[2α,4α(S*,S*)]] + [2S-[2α,4α(R*,S*)]] | R,S,S,S + S,R,S,R |
| 2ad | F | [2R-[2α,4α(S*,S*)]] + [2S-[2α,4α(S*,R*)]] | R,S,S,S + S,R,R,S |
| 2ae | F | [2R-[2α,4α(S*,S*)]] + [2R-[2α,4α(R*,S*)]] | R,S,S,S + R,S,R,S |
| 2af | F | [2R-[2α,4α(S*,S*)]] + [2R-[2α,4α(S*,S*)]] | R,S,S,S + R,S,S,S |
| 2ag | F | [2S-[2α,4α(R*,S*)]] + [2S-[2α,4α(S*,R*)]] | S,R,S,R + S,R,R,S |
| 2ah | F | [2S-[2α,4α(R*,S*)]] + [2R-[2α,4α(S*,R*)]] | S,R,S,R + R,S,S,R |
| 2ai | F | [2S-[2α,4α(S*,R*)]] + [2R-[2α,4α(R*,S*)]] | S,R,R,S + R,S,R,S |
| 2aj | F | [2R-[2α,4α(R*,S*)]] + [2R-[2α,4α(S*,R*)]] | R,S,R,S + R,S,S,R |
| 4a | Cl | [2S-[2α,4α(R*,R*)]] | S,R,S,S |
| 4b | Cl | [2S-[2α,4α(R*,S*)]] | S,R,S,R |
| 4c | Cl | [2S-[2α,4α(S*,R*)]] | S,R,R,S |
| 4d | Cl | [2S-[2α,4α(S*,S*)]] | S,R,R,R |
| 4e | Cl | [2R-[2α,4α(R*,S*)]] | R,S,R,S |
| 4f | Cl | [2R-[2α,4α(S*,R*)]] | R,S,S,R |
| 4g | Cl | [2R-[2α,4α(R*,R*)]] | R,S,R,R |
| 4h | Cl | [2R-[2α,4α(S*,S*)]] | R,S,S,S |
| 4I | Cl | [2α,4α(R*,R*)]] | S,R,S,S + R,S,R,R |
| 4j | Cl | [2α,4α(R*,S*)]] | S,R,S,R + R,S,R,S |
| 4k | Cl | [2α,4α(S*,R*)]] | S,R,R,S + R,S,S,R |
| 4l | Cl | [2α,4α(S*,S*)]] | S,R,R,R + R,S,S,S |

EXAMPLE A-3

A mixture of intermediate 2a (0.01 mol) and chloroacetyl chloride (0.0115 mol) in $CH_2Cl_2$ (200 ml) was stirred at room temperature. Pyridine (0.02 mol) was added and the mixture was stirred for 2 hours, washed with water, dried, filtered and the solvent was evaporated. The residue was crystallized from MIK/DIPE. The precipitate was filtered off and dried, yielding 6.7 g (87%) [2S-[2α,4α[(R*,R*)]]]-2-[4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-4,5-dihydro-5-oxo-1H-1,2,4-triazol-1-yl]-1-methylpropyl chloroacetate. (intern.3)

EXAMPLE A.4 a) 2,4-dihydro-4-[4-[4-(4-methoxyphenyl)-1-piperazinyl]phenyl]-3H-1,2,4-triazol-3-one (0.15 mol), prepared as described in WO94/18978, was stirred in diemthylacetamide (500 ml) at 60° C. Potassium tert-butanolate (0.165 mol) was added. The mixture was stirred at 100° C. under $N_2$ flow for I hour and then cooled to 50° C. (4R-trans)-4,5-dimethyl-2,2-dioxide-1,3,2-dioxathiolane (0.165 mol) was added dropwise. The mixture was stirred at 50° C.–60° C. for 2 hours. A concentrated $H_2SO_4$ solution (20 ml) was added dropwise. The mixture was stirred at 60° C. for 2 hours. $H_2O$ (20 ml) was added. The mixture was stirred at 60° C. for 20 hours, cooled, poured out into H₂O (1000 ml), alkalized with NaOH 50% and stirred. The precipitate was filtered off, washed with H₂O and dried. The residue was dissolved in $CH_2Cl_2/CH_3OH$. The mixture was filtered and the solvent was evaporated. The residue was triturated in 2-propanol, filtered off and dried. The residue was purified over silica gel on a glass filter (eluent: $CH_2Cl_2/CH_3OH$ 99/1). The pure fractions were collected and the solvent was evaporated. The residue was triturated in $CH_2Cl_2$ (150m1), filtered off and dried at 110° C., yielding 0.37[S-(R*,S*)7-2,4-dihydro-2-(2-hydroxy-1-methylpropyl)-4-[4-[4-(4-methoxyphenyl)-1-piperazinyl]phenyl]-3H-1,2,4-triazol-3-one (intern. 5a) $[\alpha]_{20}^D = -5.44°$ (c=19.47 mg/2 ml DMF).

b) 1-Methoxy-2-propanol (700 ml), water (700 ml) and NAOH (50%; 4.8 ml) were added to 2,4-dihydro-4-[4-[4-(4-methoxyphenyl)-1-piperazinyl]phenyl]-3H-1,2,4-triazol-3-one (0.0925 mol), prepared as described in WO94/18978. The resulting mixture was heated to 45° C. and trans-2,3-dimethyl-oxirane (0.1387 mol) was added, while stirring at 45° C. The reaction mixture was stirred for 68 hours at 45° C. and for 60 hours at 60° C., then cooled to 20° C. More NaOH (50%; 4.8 ml) was added. The reaction mixture was stirred for 64 hours at 50° C., for 18 hours at 100° C., then cooled on an ice-bath. The mixture was filtered, giving precipitate (1) and filtrate (2). Precipitate (1) was dried and redissolved in $CH_2Cl_2$ (100 ml), filtered off. The corresponding filtrate was evaporated and the residue was dried, yielding 2.2 g (R*,S*)-2,4-dihydro-2-(2-hydroxy-1-methylpropyl)-4-[4-[4-(4-methoxyphenyl)-1-piperazinyl]phenyl]-3H-1,2,4-triazol-3-one (interm. 5b). Filtrate (2) was evaporated. The residue was stirred in CH₂Cl, (150 ml) and filtered off. The corresponding filtrate was evaporated and the residue was dried, yielding 7.4 g (R*,S*)-2,4-dihydro-2-(2-hydroxy-1-methylpropyl)-4-[4-[4-(4-methoxyphenyl)-1-piperazinyl]phenyl]-3H-1,2,4-triazol-3-one (interm. 5b). The two fractions of intermediate 5b were combined and further purified using activated charcoal, column chromatography and recrystallization, yielding 1.5 g (3.9% overall yield) of (R*,S*)-2,4-dihydro-2-(2-hydroxy-1-methylpropyl)-4-[4-[4-(4-methoxyphenyl)-1-piperazinyl]phenyl]-3H-1,2,4-triazol-3-one (interm. 5b).

EXAMPLE A-5

A mixture of intermediate 5a (0.00327 mol), triphenylphosphine (0.00806 mol) and p-nitrobenzoic acid (0.00717 mol) in tetrahydrofuran/dimethylacetamide 3/2 (50 ml) was heated until complete dissolution. Then diethyl azodicarboxylate (0.00806 mol) was added dropwise. The mixture was stirred at room temperature for 90 minutes and at 50° C. for 1 hour. A NaOH solution (1N; 10 m]) was added at 50° C. The mixture was poured out into water (100 ml) and NaOH (1N; 90 ml) and then stirred. The precipitate was filtered off and recrystallized from 2-propanol (60 ml). The mixture was stirred for 48 hours. The precipitate was filtered off and dried, yielding 0.98 g (71%) of [S-(R* ,R *)] -2, 4-dihydro-2-(2-hydroxy-1-methylpropyl)-4-[4-[4-(4-methoxyphenyl)-1-piperazinyl]phenyl]-3H-1,2,4-triazol-3-one (interm. 5c).

EXAMPLE A-6 a) N,N-dimethyl-4-pyridinamine (0.01062 mol) and intermediate 5a (0.00708 mol) were suspended in $CH_2Cl_2$ (50 ml). A solution of methanesulfonylchloride (0.01062 mol) in $CH_2Cl_2$ (30 ml) was added dropwise at room temperature. The mixture was stirred at room temperature for the weekend. N,N-dimethyl-4-pyridinamine (0.00352 mol) and methanesulfonylchloride (0.00358 mol) were added again. The mixture was stirred overnight, washed with water (2×100 ml), dried, filtered over decalite and the solvent was evaporated. The residue was dissolved in MIK (150 ml). Activated charcoal (0.5 g) was added. The mixture was boiled, filtered warm and stirred for 2 hours. The precipitate was filtered off and dried, yielding 1.7 g (50%) of [S-(R*, S*)]-2,4-dihydro-2-(2-methanesulfonyloxy-1-methylpropyl)-4-[4-[4-(4-methoxyphenyl)-1-piperazinyl] phenyl]-3H-1,2,4-triazol-3-one (interm. 5d).

b) According to the precedure described in Nakamura et al. (J.A.C.S. 1985, 107 p2138), intermediate 5d (0.001 mol) was added to a solution of KOH (0.03 g) in $CH_3OH$ (7 ml) and tetrahydrofuran (3 ml). The mixture was stirred at 100° C. for 4 hours, yielding [S-(R*,R*)]-2,4-dihydro-2-(2-hydroxy-1-methylpropyl)-4-[4-[4-(4-methoxyphenyl)-1-piperazinyl]phenyl]-3H-1,2,4-triazol-3-one (interm. 5c).

B. Preparation of the Final Compounds

EXAMPLE B-1

A mixture of N-[(1,1-dimethylethoxy)carbonyl]-L-phenylalanine (0.023 mol), intermediate (2a) (0.01 mol), dicyclohexylcarbodiimide (0.046 mol) and N,N-dimethyl-4-pyridinamine (0.046 mol) in $CH_2Cl_2$ (200 ml) was stirred at room temperature overnight. Water (200 ml) was added and the mixture was stirred for 1 hour and extracted with $CH_2Cl_2$. The organic layer was separated, washed with water, dried, filtered and the solvent was evaporated. The residue was purified by column chromatography over silica gel (eluent: $CH_2Cl_2/CH_3OH$ 99/1). The pure fractions were collected and the solvent was evaporated, yielding 10.8 g (86.7%) [2S-[2α,4α-[(R*,R*)]]]-2-[4-[4-[4-[4-[[2-(2,4-difluorophenyl)-2-(1H-1,2,4-triazol-1-ylmethyl)-1,3-dioxolan-4-yl]methoxy]-phenyl]-1-piperazinyl]phenyl]-4,5-dihydro-5-oxo-1H-1,2,4-triazol-1-yl]-1-methylpropyl N-[(1,1-dimethylethoxy) (compound 22).

EXAMPLE B-2 a) A mixture of compound 22 (0.0075 mol) in trifluoroacetic acid (15 ml) and $CH_2Cl_2$ (150ml) was stirred overnight. The mixture was poured out into a $NaHCO_3$ solution, stirred for 30 minutes and extracted with $CH_2Cl_2$. The organic layer was separated, washed, dried, filtered and the solvent was evaporated. The residue was purified by flash column chromatography over silica gel (eluent: $CH_2Cl_2/CH_3OH$ 96/4). The pure fractions were collected and the solvent was evaporated. The residue was triturated in DIPE. The precipitate was filtered off and dried, yielding 3.6 g [2S-[2α,4α[(R*,R*)]]]-2-[4-[4-[4-[4-[[2-(2,4-difluorophenyl)-2-(1H-1,2,4-triazol-1-ylmethyl)-1,3-dioxolan-4-yl]methoxy]-phenyl]-1-piperazinyl]-phenyl]-4,5-dihydro-5-oxo-1H-1,2,4-triazol-1-yl]-1-methylpropyl L-phenylalanine (compound 23).

b) Compound 23 (0.00359 mol) was dissolved in 2-propanone (25 ml). A solution of (Z)-2-butenedioic acid (0.00359 mol) in 2-propanone (5 ml) was added. The mixture was stirred for 16 hours. The precipitate was filtered off, washed with 2-propanone (2.5 ml), and dried, yielding 3.12 g [2S-[2α,4α[(R*,R*)]]]-2-[4-[4-[4-[4-[[2-(2,4-difluorophenyl)-2-(1H-1,2,4-triazol-1-ylmethyl)-1,3-dioxolan-4-yl]methoxy]-phenyl]-1-piperazinyl]-phenyl]-4,5-dihydro-5-oxo-1H-1,2,4-triazol-1-yl]-1-methylpropyl L-phenylalanine (Z)-2-butenedioate (1:1) (compound 25).

EXAMPLE B-3

A mixture of intermediate (3) (0.0081 mol) and N,N-diethylamine (0.027 mol) in DMF (50 ml) was stirred at room temperature for 8 hours. The mixture was allowed to stand for 5 days, then poured out into water and extracted with CH$_2$Cl$_2$. The organic layer was separated, washed with water, dried, filtered and the solvent was evaporated. The residue was purified by column chromatography over silica gel (eluent: CH$_2$Cl$_2$/CH$_3$OH 98/2). The pure fractions were collected and the solvent was evaporated. The residue was dissolved in CH$_3$CN (200 ml) and converted into the (E)-2-butenedioic acid salt (1:1). The precipitate was filtered off and dried, yielding 5 g (67%) [2S-[2α,4α-[(R*,R*)]]]-2-[4-[4-[4-[4-[[2-(2,4-difluorophenyl)-2-(H-1,2,4-triazol-1-ylmethyl)-1,3-dioxolan-4-yl]methoxy]phenyl]-1-piperazinyl]phenyl]-4,5-dihydro-5-oxo-1H-1,2,4-triazol-1-yl]-1-methylpropyl N,N-diethylglycine (E)-2-butenedioate (compound 16).

EXAMPLE B-4

[2S-[2α,4[(R*,R*)]]]-2-[4-[4-[4-[4-[[2-(2,4-difluorophenyl)-2-(1H-1,2,4-triazol-ylmethyl)-1,3-dioxolan-4-yl]methoxy]phenyl]-1-piperazinyl]phenyl]-4,5-dihydro-5-oxo-1H-1,2,4-triazol-1-yl]-1-methylpropyl β-alanine (0.0028 mol) was dissolved in warm ethanol (25 ml). (−)-(S)-hydroxybutanedioic acid (0.0061 mol) was added and the mixture was parboiled until complete dissolution. The resulting clear solution was allowed to cool to room temperature and the solvent was evaporated. The residue was stirred in 2-propanone, filtered off, then dried, yielding 1.53 g (53%) [2S-[2α,4α-[(R*,R*)]]]-2-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-4,5-dihydro-5-oxo-1H-1,2,4-triazol-1-yl]-1-methylpropyl β-alanine (S)-hydroxybutanedioate(1:2) monohydrate (compound 12).

Table 3 lists the compounds of formula (I) that were prepared according to one of the above examples referred to in the column "Ex. No.".

TABLE 3

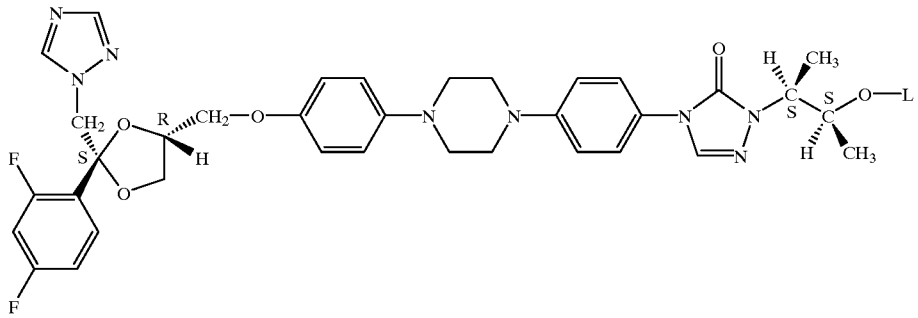

| Co. No. | Ex. No. | -O-L | addition salt |
|---|---|---|---|
| 1 | B.1 | N-((1,1-dimethylethyl)oxycarbonyl)-β-alanine ester | — |
| 2 | B.2a | β-alanine ester | fumaric acid (2:3) |
| 3 | B.1 | N-((1,1-dimethylethyl)oxy-carbonyl)-glycine ester | — |
| 4 | B.2a | glycine ester | fumaric acid (1:1) |
| 5 | B.2a | β-alanine ester | succinic acid (1:2) |
| 6 | B.2a | β-alanine ester | succinic acid (1:1) |
| 7 | B.2a | glycine ester | succinic acid (1:2) |
| 8 | B.1 | N-((1,1-dimethylethyl)oxy-carbonyl)-L-alanine ester | — |
| 9 | B.1 | N-((1,1-dimethylethyl)oxy-carbonyl)-L-leucine ester | — |
| 10 | B.2a | L-alanine ester | succinic acid (1:1). hydrate (1:1) |
| 11 | B.2a | β-alanine ester | — |
| 12 | B.4 | β-alanine ester | L-malic acid (1:2). hydrate (1:1) |
| 13 | B.4 | β-alanine ester | oxalic acid (2:3). hydrate (1:2) |
| 14 | B.1 | N-((1,1-dimethylethyl)oxycarbonyl)-L-phenyl-glycine ester | — |
| 15 | B.1 | N,N-diethyl-β-alanine ester | fumaric acid (2:3). hydrate (1:1) |
| 16 | B.3 | N,N-diethyl-glycine ester | fumaric acid (1:1) |
| 17 | B.1 | N-((1,1-dimethylethyl)oxycarbonyl)-L-valine ester | — |
| 18 | B.2a | L-valine ester | — |
| 19 | B.4 | β-alanine ester | maleic acid (1:2) |
| 20 | B.4 | β-alanine ester | L-tartaric acid (1:2) |
| 21 | B.2a | L-leucine ester | — |
| 22 | B.1 | N-((1,1-dimethylethyl)oxy-carbonyl)-L-phenyl-alanine ester | — |
| 23 | B.2a | L-phenylalanine ester | — |
| 24 | B.2a | L-phenylglycine ester | — |
| 25 | B.2b | L-phenylalanine ester | maleic acid (1:1) |

TABLE 3-continued

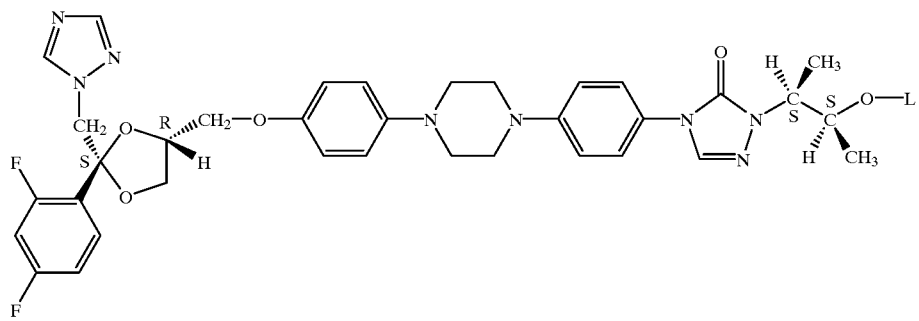

| Co. No. | Ex. No. | -O-L | addition salt |
|---|---|---|---|
| 26 | B.2b | L-phenylalanine ester | HCl (1:1) |
| 27 | B.1 | N-((1,1-dimethylethyl)oxy-carbonyl)-D-phenyl-alanine ester | — |
| 28 | B.2a | D-phenylalanine ester | — |
| 29 | B.3 | N,N-diethyl-glycine ester | — |

TABLE 4

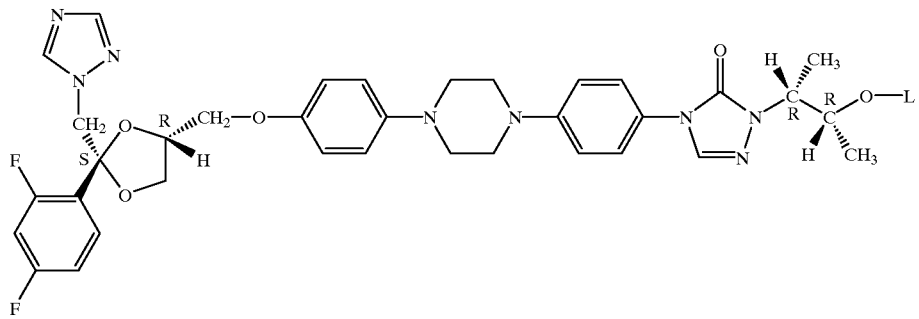

| Co. No. | Ex. No. | -O-L |
|---|---|---|
| 30 | B.1 | N-((1,1-dimethylethyl)oxy-carbonyl)-L-phenyl-alanine ester |
| 31 | B.2a | L-phenylalanine ester |

Table 5 lists both the experimental (column heading "exp") and theoretical (column heading "theor") elemental analysis values for carbon, hydrogen and nitrogen of the compounds as prepared in the experimental part hereinabove.

TABLE 5

| Comp. No. | Carbon | | Hydrogen | | Nitrogen | |
|---|---|---|---|---|---|---|
| | exp | theor | exp | theor | exp | theor |
| 1 | 59.85 | 60.06 | 5.92 | 5.98 | 14.6 | 14.66 |
| 2 | 56.6 | 56.59 | 5.3 | 5.29 | 13.54 | 13.5 |
| 3 | 59.66 | 59.64 | 6.05 | 5.84 | 15.17 | 14.9 |
| 4 | 56.89 | 57.14 | 5.32 | 5.26 | 14.35 | 14.63 |
| 5 | 55.33 | 55.47 | 5.54 | 5.57 | 12.48 | 12.66 |
| 6 | 56.64 | 57.46 | 5.73 | 5.63 | 13.68 | 14.36 |
| 7 | 54.95 | 55.04 | 5.43 | 5.44 | 12.65 | 12.84 |
| 8 | 59.95 | 60.06 | 5.97 | 5.98 | 14.62 | 14.66 |
| 9 | 61.01 | 61.25 | 6.31 | 6.37 | 13.89 | 13.98 |
| 10 | 56.43 | 56.31 | 5.6 | 5.74 | 14.09 | 14.07 |
| 14 | 62.25 | 62.53 | 5.87 | 5.79 | 13.33 | 13.67 |
| 15 | 57.28 | 57.19 | 5.64 | 5.9 | 12.37 | 12.51 |
| 17 | 61.87 | 60.87 | 6.86 | 6.24 | 13.99 | 14.2 |
| 18 | 60.66 | 60.98 | 5.89 | 6.01 | 15.96 | 16 |
| 21 | 61.14 | 61.41 | 6.14 | 6.16 | 15.66 | 15.72 |
| 22 | 64.02 | 62.88 | 6.98 | 5.92 | 13.18 | 13.47 |
| 23 | 62.69 | 63.22 | 5.8 | 5.67 | 14.9 | 15.08 |
| 24 | 62.43 | 62.84 | 5.47 | 5.52 | 15.41 | 15.34 |
| 26 | 60.79 | 60.58 | 5.64 | 5.55 | 14.39 | 14.45 |

TABLE 5-continued

| Comp. | Carbon | | Hydrogen | | Nitrogen | |
|---|---|---|---|---|---|---|
| No. | exp | theor | exp | theor | exp | theor |
| 28 | 62.56 | 63.22 | 5.49 | 5.67 | 14.84 | 15.08 |
| 29 | 61.35 | 61.41 | 6.15 | 6.16 | 15.82 | 15.72 |
| 31 | 62.41 | 62.45 | 5.82 | 5.65 | 14.81 | 14.57 |

C. Physicochemical Example

EXAMPLE C-1

Solubility

An excess of compound was added to the solvent (the type of solvent is specified in table 6). The mixture was shaken during 1 day at room temperature. The precipitate was filtered off. The pH of the remaining solvent was measured and is shown in the table. The concentration of the compound was measured via HPLC and is shown in the column "Solubility".

TABLE 6

| Co. No. | Solvent | pH | Solubility (mg/ml) |
|---|---|---|---|
| 10 | 0.1M HCl | 1.34 | >6.20 |
|  | 0.0001M HCl | 4.40 | 2.84 |
| 12 | 0.1M HCl | 1.34 | >6.94 |
|  | 0.0001M HCl | 3.76 | 3.28 |
| 13 | 0.1M HCl | 1.29 | >6.08 |
|  | 0.0001M HCl | 3.17 | 2.95 |
| 15 | 0.1M HCl | 1.30 | >6.32 |
|  | 0.0001M HCl | 3.59 | 5.50 |
| 16 | 0.1M HCl | 1.23 | >6.17 |
|  | 0.000M HCl | 3.94 | 3.85 |
| 18 | 0.1M HCl | 1.26 | >5.30 |
|  | 0.0001M HCl | 6.29 | 0.05 |
| 21 | 0.1M HCl | 1.35 | >5.25 |
|  | 0.0001M HCl | 6.68 | 0.11 |
| 23 | 0.1M HCl | 1.37 | >5.56 |
|  | 0.0001M HCl | 5.97 | 0.02 |
| 24 | 0.1M HCl | 1.38 | >5.49 |
|  | 0.0001M HCl | 5.83 | 0.014 |
| 25 | 0.1M HCl | 1.45 | >6.44 |
|  | 0.0001M HCl | 4.40 | 0.67 |
| 26 | 0.1M HCl | 1.50 | >6.37 |
|  | 0.0001M HCl | 4.00 | 4.64 |
| 28 | 0.1M HCl | 1.50 | 10.89 |
|  | 0.0001M HCl | 4.55 | 0.19 |
|  | 0.1M HCl | 1.55 | >5.84 |
|  | 0.0001M HCl | 4.90 | 0.069 |

EXAMPLE C-2

Chemical Stability 50 mg of test compound was placed in an open glass jar at 40° C. and 75% relative humidity. After one week, the amount of test compound remaining was determined.

TABLE 7

| Co. No. | Stability |
|---|---|
| 10 | 31.0% |
| 12 | 96.1% |
| 13 | 98.3% |
| 15 | 90.4% |
| 16 | 100.3% |
| 18 | 101.7% |

TABLE 7-continued

| Co. No. | Stability |
|---|---|
| 21 | 100.3% |
| 23 | 99.7% |
| 24 | 101.2% |

D. Pharmacological Examples

EXAMPLE D-1

Determination of Fungal Susceptibility

A panel of Candida isolates plus single isolates of the dermatophytes *Microsporum canis, Trichophyton rubrum* and *T. mentagrophytes; Aspergillus fumigates,* and *Cryptococcus neoformans* were used to evaluate the activity of the test compounds in vitro. Inocula were prepared as broth cultures (yeasts) or as suspensions of fungal material made from agar slope cultures (moulds). The test compounds were pipetted from DMSO stock solution into water to provide a series of 10-fold dilutions. The fungal inocula were suspended in the growth medium CYG (F.C. Odds, Journal of Clinical Microbiology, 29, (2735-2740, 1991) at approximately 50,000 colony-forming units (CFU) per ml and added to the aqueous test drugs.

The cultures were set up in the 96 wells of plastic microdilution plates and they were incubated for 2 days at 37° C. (Candida spp.) or for 5 days at 30° C. (other fungi). Growth in the microcultures was measured by their optical density (OD) measured at a wavelength of 405 nm. The OD for cultures with test compounds was calculated as a percentage of the control, drug-free OD. Inhibition of growth to 35% of control or less was recorded as significant inhibition.

Minimal inhibitory concentration (MICs; in $10^{-6}$ M) of intermediate 2 as the major metabolite and some of the compounds of formula (I) for *Candida glabrata, Candida krusei, Candida parapsilosis, Candida albicans, Candida kefyr, Candida tropicalis, Microsporum canis, Trichophyton rubrum, Trichophyton mentagrophytes, Cryptococcus neoformans, Aspergillus fumigatus* are listed in table 8.

TABLE 8

| | MIC values in $10^{-6}$M | | | | |
|---|---|---|---|---|---|
| | | | Co. No. | | |
| infection | Interm. 2a | 16 | 18 | 21 | 23 |
| Candida glabrata | 10 | 10 | 10 | 10 | 10 |
| Candida krusei | 1 | 1 | 1 | 1 | 1 |
| Candida parapsilosis | 1 | <0.1 | <0.1 | 0.1 | <0.1 |
| Candida albicans | 10 | <0.1 | <0.1 | 0.1 | <0.1 |
| Candida kefyr | <0.1 | <0.1 | <0.1 | 0.1 | <0.1 |
| Candida tropicalis | 1 | <0.1 | <0.1 | 0.1 | <0.1 |
| Microsporum canis | 1 | 1 | 10 | 1 | <1 |
| Trichophyton rubrum | 1 | <0.1 | 10 | <0.1 | <0.1 |
| Trichophyton mentagrophytes | 1 | 1 | 1 | 1 | 1 |
| Cryptococcus neoformans | 1 | 1 | 1 | 1 | 1 |
| Aspergillus fumigatus | 1 | 1 | 1 | 1 | 1 |

EXAMPLE D-2

Disseminated Aspergillosis and Candidosis in Guinea-pigs

Specific pathogen-free (SPF) guinea-pigs (weighing 400-500 g) were used in all experiments. A catheter was placed into the left jugular vein of the animals that were treated by intravenous infusion, the vein was ligated, and the catheter was connected to a microprocessor-controlled infusion pump. The animals were infected with *Aspergillus fumigatus* (4,000 CFU/g body weight) or with *Candida albicans* (40,000 CFU/g body weight) either via the lateral vein of the penis or via the implanted catheter. Intravenous treatments (5 mg/kg/day) began I hour after infection. The test formulations were then administered on subsequent days as two, I hour infusions daily, separated by a period of 5 hours, for a total of 19 infusions or 9.5 days. Oral treatments with the test compounds (5 mg/kg/day) begun I hour after infection and were repeated twice daily up to the tenth day after infection (a total of 19 treatments. For each group of tested animals (number of tested animals per group given in column "N"), the mean survival time (MST) in days was recorded as well as the % survivors (% surv). Animals of each group which died during the experiment and those that survived the experiment and were killed, were investigated for counts of *Aspergillus fumigatus* and *Candida albicans* in deep tissue (liver, spleen, kidney, lung and brain) post mortem. The remaining CFU/g in the culture-positive livers was measured and expressed in table 9 (after intravenous treatment) and table 10 (after oral treatment) as mean $\log_{10}$ CFU/g. The columns "%neg" in tables 9 and 10 express the total percentage culture-negative deep tissues after the treatment. Hence, the more effective test compounds have a high value in the "MST", "%surv" and "%neg" columns, and a low value in the "CFU/g" columns.

E. Composition Example

EXAMPLE E.1

Injectable solution 1.8 Grams methyl 4-hydroxybenzoate and 0.2 grams sodium hydroxide were dissolved in about 0.5 l of boiling water for injection. After cooling to about 50° C. there were added while stirring 0.05 grams propylene glycol and 4 grams of the active ingredient.

The solution was cooled to room temperature and supplemented with water for injection q.s. ad 1 l, giving a solution comprising 4 mg/ml of active ingredient. The solution was sterilized by filtration and filled in sterile containers.

What is claimed is:

1. A compound of formula (I),

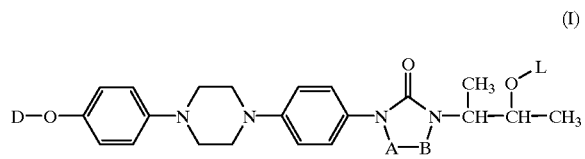

(I)

a N-oxide form, a pharmaceutically acceptable addition salt or a stereochemically isomeric form thereof, wherein —A—B— forms a bivalent radical of formula

| —N=CH— | (a), |
| —CH=N— | (b), |
| —CH=CH— | (c), | wherein one hydrogen atom in the radicals (a) and (b) may be replaced with a $C_{1-6}$-alkyl-radical and up to two hydrogen atoms in radical (c) may be replaced by a $C_{1-6}$-alkyl-radical; L represents the acyl moiety of an amino acid such that —O-L represents an amino acid ester group;

TABLE 9

| | *Aspergillus fumigatus* (i.v. treatment) | | | | *Candida albicans* (i.v. treatment) | | | | |
|---|---|---|---|---|---|---|---|---|---|
| Co. No. | N | MST (days) | % surv | CFU/g (liver) | % neg | N | MST (days) | % surv | CFU/g (liver) | % neg |
| placebo | 6 | 4.8 | 0 | 4.4 | 13 | 10 | 3.9 | 0 | 3.8 | 2 |
| 16 | 6 | 6.8 | 16.7 | 3.4 | 29 | 10 | 9.3 | 66.7 | 0 | 79 |
| 18 | 6 | 5.3 | 16.7 | 3.1 | 29 | 10 | 9.2 | 66.7 | 0 | 92 |
| 21 | 6 | 5.7 | 0 | 3.7 | 46 | 10 | 6.5 | 16.7 | 2.7 | 75 |
| 23 | 6 | 9.2 | 83.3 | 3.6 | 71 | 10 | 9.8 | 83.3 | 0 | 79 |

TABLE 10

| | *Aspergillus fumigatus* (oral treatment) | | | | *Candida albicans* (oral treatment) | | | | |
|---|---|---|---|---|---|---|---|---|---|
| Co. No. | N | MST (days) | % surv | CFU/g (liver) | % neg | N | MST (days) | % surv | CFU/g (liver) | % neg |
| placebo | 10 | 4.3 | 0 | 4.0 | 5 | 10 | 4.2 | 0 | 3.2 | 8 |
| 16 | 10 | 6.5 | 40 | 3.1 | 48 | 10 | 9.6 | 90 | 0 | 73 |
| 18 | 10 | 5.2 | 0 | 3.2 | 20 | 10 | 10 | 100 | 0 | 68 |
| 21 | 10 | 7.0 | 40 | 3.0 | 55 | 10 | 9.6 | 90 | 0 | 83 |
| 23 | 10 | 7.8 | 30 | 3.0 | 55 | 10 | 10 | 100 | 0 | 73 |

D is a radical of formula

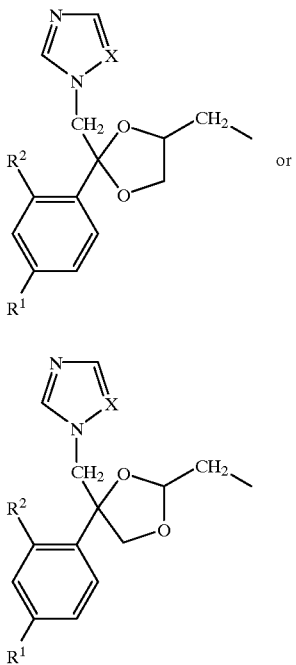

wherein
X is N or CH;
$R^1$ is halo;
$R^2$ is hydrogen or halo.

2. A compound according to claim 1 wherein L represents a radical of formula (a)

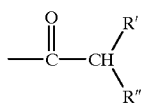

wherein
R' represents amino; mono- or di($C_{1-6}$alkyl)amino; amino$C_{1-6}$alkyl;

$C_{1-6}$alkyloxycarbonylamino; benzyloxycarbonylamino; trifluoromethoxycarbonylamino; 1-pyrrolidinyl; 1-piperidinyl; 4-morpholinyl;

1-piperazinyl or 1-piperazinyl substituted with $C_{1-6}$alkyl, hydroxy$C_{1-6}$alkyl, amino$C_{1-6}$alkyl or $C_{1-6}$alkylamino$C_{1-6}$alkyl;

R" represents hydrogen; $C_{1-6}$alkyl; aryl; $C_{1-6}$alkyl substituted with aryl, $C_{1-6}$alkylthio, indolyl, amino, hydroxy, mercapto, aminocarbonyl, carboxyl, guanidinyl, imidazolyl; or R' and R" taken together form —$CH_2$—$CH_2$—$CH_2$—NH—;

aryl is phenyl or phenyl substituted with hydroxy or halo.

3. A compound according to claim 2 wherein L represents the acyl moiety selected from:

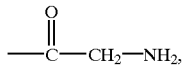 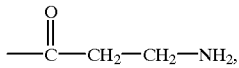

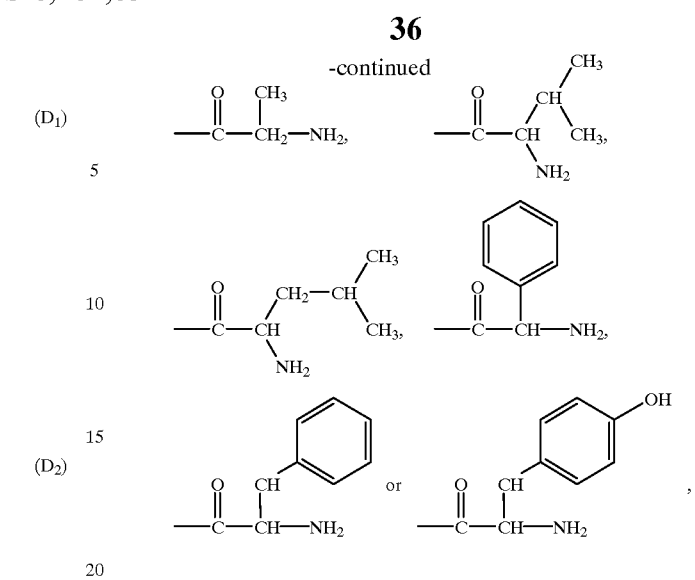

or those derivatives thereof in which the amino moiety is mono- or disubstituted with $C_{1-6}$alkyl or monosubstituted with tert-butyloxycarbonyl.

4. A compound according to claim 3 wherein the substituents on the dioxolane ring have the cis configuration.

5. A compound according to claim 4 wherein D is a radical of formula D1.

6. A compound according to claim 5 wherein $R^1$ and $R^2$ are fluoro, X is N and —A—B— is a radical of formula (b).

7. A compound according to claim 4 wherein the two chiral carbons of the 1-methylpropyl moiety both have the S configuration, and D is a radical of formula D1 wherein the substituents on the dioxolane ring have a cis configuration and carbon atom number 2 of the dioxolane ring has an absolute S configuration.

8. A compound according to claim 1 wherein the compound is

2-[4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-4,5-dihydro-5-oxo-1H-1,2,4-triazol-1-yl]-1-methylpropyl N,N-diethylglycine;

2-[4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]-phenyl]-4,5-dihydro-5-oxo-1H-1,2,4-triazol-1-yl]-1-methylpropyl L-phenylalanine;

2-[4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]-phenyl]-4,5-dihydro-5-oxo-1H-1,2,4-triazol-1-yl]-1-methylpropyl L-leucine;

2-[4-[4-[4-[4-[[2-(2,4-difluorophenyl)-2-(1H-1,2,4-triazol-1-ylmethyl)-1,3-dioxolan-4-yl]methoxy]-phenyl] -1-piperazinyl]-phenyl]-4,5-dihydro-5-oxo-1H-1,2,4-triazol-1-yl]-1-methylpropyl L-valine;

2-[4-[4-[4-[4-[[2-(2,4-difluorophenyl)-2-(1H-1,2,4-triazol-1-ylmethyl)-1,3-dioxolan-4-yl]methoxy]-phenyl]-1-piperazinyl]-phenyl]-4,5-dihydro-5-oxo-1H-1,2,4-triazol-1-yl]-1-methylpropyl L-phenylglycine; a N-oxide form, a pharmaceutically acceptable addition salt thereof or a stereochemical isomeric form thereof.

9. A pharmaceutical composition comprising a pharmaceutically acceptable carrier, and as active ingredient a therapeutically effective amount of a compound as claimed in claim 1.

10. A pharmaceutical composition according to claim 9 suitable for intravenous administration.

11. A process of preparing a pharmaceutical composition, comprising mixing a pharmaceutically acceptable carrier with a therapeutically effective amount of a compound as claimed in claim 1.

12. A process of preparing a compound as claimed in claim 1, characterized by a) O-acylation of an intermediate alcohol of formula (II) with an acylating reagent of formula (III),

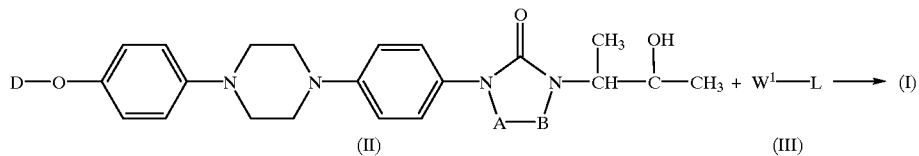

wherein W¹ is a reactive leaving group connected to the acyl moiety of L, and L, D and —A—B— are as defined in claim 1; by stirring the reactants in a reaction-inert solvent, optionally in admixture with a base to pick up the acid which is formed during the reaction;

b) O-alkylating a phenol of formula (IV) with an alkylating reagent of formula (V),

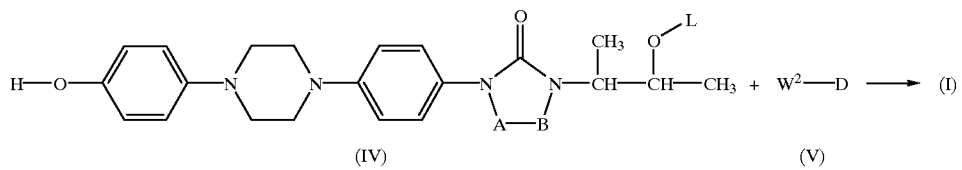

wherein $W^2$ is a reactive leaving group and D, —A—B— and L are as defined in claim 1, by stirring the reactants in a reaction-inert solvent, optionally in admixture with a suitable base to pick up the acid which is formed during the reaction;

c) O-acylating an intermediate of formula (II) with a reagent of formula (VI) and subsequently reacting the thus obtained intermediate of formula (VII) with an amine of formula (VIII),

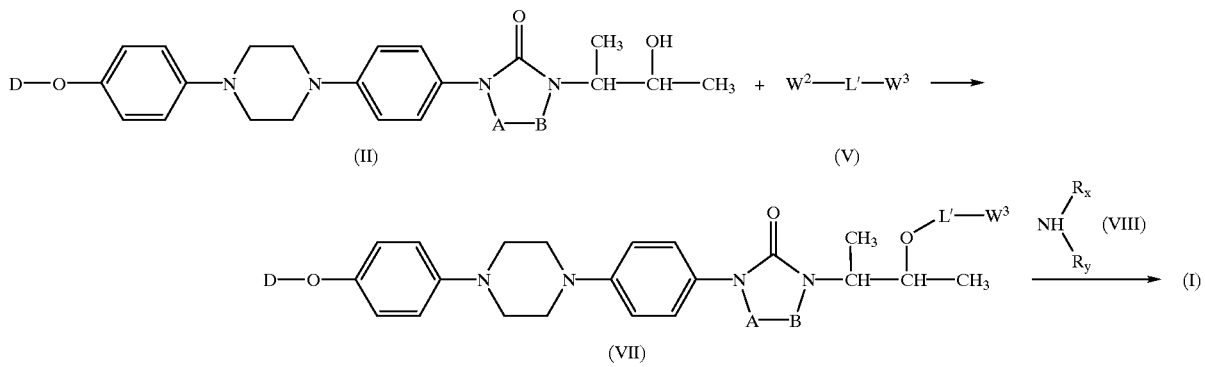

wherein $W^3$ is a reactive leaving group, D and —A—B— are as defined in claim 1, $NR_xR_y$ is an optionally mono- or disubstituted amino moiety of the amino acid as defined by L in claim 1, L' identical to L as defined in claim 1 wherein $R_x$ and $R_y$ are hydrogen, $C_{1-6}$ alkyl or an amino protecting group;

and further, if desired, converting the compounds of formula (I), into a therapeutically active non-toxic acid addition salt by treatment with an acid, or conversely, converting the acid addition salt form into the free base by treatment with alkali; and, if desired, preparing stereochemically isomeric forms or N-oxide forms thereof.

13. A method of treating fungal infections in a warm-blooded animal in need thereof comprising administering to the animal an effective amount of the compound of claim 1.

* * * * *